United States Patent
DeFreitas et al.

(10) Patent No.: US 9,066,706 B2
(45) Date of Patent: *Jun. 30, 2015

(54) INTEGRATED MULTI-MODE MAMMOGRAPHY/TOMOSYNTHESIS X-RAY SYSTEM AND METHOD

(71) Applicant: Hologic, Inc., Bedford, MA (US)

(72) Inventors: Kenneth DeFreitas, Patterson, NY (US);
Thomas Farbizio, Newtown, CT (US);
Baorui Ren, Andover, MA (US);
Christopher Ruth, Boxford, MA (US);
Ian Shaw, Yorktown Heights, NY (US);
Andrew P. Smith, Lexington, MA (US);
Jay Stein, Boston, MA (US)

(73) Assignee: Hologic, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/058,385

(22) Filed: Oct. 21, 2013

(65) Prior Publication Data
US 2014/0044231 A1  Feb. 13, 2014

Related U.S. Application Data

(63) Continuation of application No. 13/462,342, filed on May 2, 2012, now Pat. No. 8,565,374, which is a continuation of application No. 12/954,971, filed on Nov. 29, 2010, now Pat. No. 8,175,219, which is a
(Continued)

(51) Int. Cl.
*A61B 6/04* (2006.01)
*A61B 6/02* (2006.01)
(Continued)

(52) U.S. Cl.
CPC ............... *A61B 6/502* (2013.01); *A61B 6/4417* (2013.01); *A61B 6/107* (2013.01); *A61B 6/482* (2013.01); *A61B 6/4291* (2013.01); *A61B 6/025* (2013.01); *A61B 6/0414* (2013.01)

(58) Field of Classification Search
CPC ........ A61B 6/025; A61B 6/04; A61B 6/0414; A61B 6/44; A61B 6/4411; A61B 6/4417; A61B 6/4429; A61B 6/4435; A61B 6/4441; A61B 6/502
USPC .................. 378/21–27, 37, 62, 114–116, 210
See application file for complete search history.

(56) References Cited

U.S. PATENT DOCUMENTS

| | | |
|---|---|---|
| 3,502,878 A | 3/1970 | Stewart |
| 3,863,073 A | 1/1975 | Wagner |

(Continued)

FOREIGN PATENT DOCUMENTS

| | | |
|---|---|---|
| EP | 0775467 | 5/1997 |
| EP | 0982001 | 3/2000 |

(Continued)

OTHER PUBLICATIONS

Observations by Third Party, Remarks concerning European patent application No. 10707751.3 according to Article 115 EPC, dated Apr. 24, 2014, 8 pgs.

(Continued)

*Primary Examiner* — Anastasia Midkiff

(57) ABSTRACT

A system for multi-mode breast x-ray imaging which comprises a compression arm assembly for compressing and immobilizing a breast for x-ray imaging, an x-ray tube assembly, and an x-ray image receptor is provided. The system is configured for a plurality of imaging protocols and modes.

19 Claims, 16 Drawing Sheets

Related U.S. Application Data continuation of application No. 11/791,601, filed as application No. PCT/US2005/042613 on Nov. 23, 2005, now Pat. No. 7,869,563.

(60) Provisional application No. 60/631,296, filed on Nov. 26, 2004.

(51) Int. Cl.
*A61B 6/00* (2006.01)
*A61B 6/10* (2006.01)

(56) References Cited

U.S. PATENT DOCUMENTS

| | | |
|---|---|---|
| 3,971,950 A | 7/1976 | Evans et al. |
| 4,160,906 A | 7/1979 | Daniels et al. |
| 4,310,766 A | 1/1982 | Finkenzeller et al. |
| 4,496,557 A | 1/1985 | Malen et al. |
| 4,513,433 A | 4/1985 | Weiss et al. |
| 4,559,641 A | 12/1985 | Caugant et al. |
| 4,706,269 A | 11/1987 | Reina et al. |
| 4,744,099 A | 5/1988 | Huettenrauch et al. |
| 4,773,086 A | 9/1988 | Fujita et al. |
| 4,773,087 A | 9/1988 | Plewes |
| 4,819,258 A | 4/1989 | Kleinman et al. |
| 4,821,727 A | 4/1989 | Levene et al. |
| 4,969,174 A | 11/1990 | Scheid et al. |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,129,911 A | 7/1992 | Siczek et al. |
| 5,163,075 A | 11/1992 | Lubinsky et al. |
| 5,164,976 A | 11/1992 | Scheid et al. |
| 5,199,056 A | 3/1993 | Darrah |
| 5,219,351 A | 6/1993 | Teubner |
| 5,240,011 A | 8/1993 | Assa |
| 5,289,520 A | 2/1994 | Pellegrino et al. |
| 5,359,637 A | 10/1994 | Webber |
| 5,365,562 A | 11/1994 | Toker |
| 5,415,169 A | 5/1995 | Siczek et al. |
| 5,426,685 A | 6/1995 | Pellegrino et al. |
| 5,452,367 A | 9/1995 | Bick et al. |
| 5,506,877 A | 4/1996 | Niklason et al. |
| 5,526,394 A | 6/1996 | Siczek et al. |
| 5,539,797 A | 7/1996 | Heidsieck et al. |
| 5,553,111 A | 9/1996 | Moore et al. |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzke et al. |
| 5,609,152 A | 3/1997 | Pellegrino et al. |
| 5,627,869 A | 5/1997 | Andrew et al. |
| 5,657,362 A | 8/1997 | Giger et al. |
| 5,668,844 A | 9/1997 | Webber |
| 5,668,889 A | 9/1997 | Hara |
| 5,706,327 A | 1/1998 | Adamkowski et al. |
| 5,719,952 A | 2/1998 | Rooks |
| 5,735,264 A | 4/1998 | Siczek et al. |
| 5,769,086 A | 6/1998 | Ritchart et al. |
| 5,773,832 A | 6/1998 | Sayed et al. |
| 5,803,912 A | 9/1998 | Siczek et al. |
| 5,818,898 A | 10/1998 | Tsukamoto et al. |
| 5,828,722 A | 10/1998 | Ploetz et al. |
| 5,872,828 A | 2/1999 | Niklason et al. |
| 5,878,104 A | 3/1999 | Ploetz |
| 5,896,437 A | 4/1999 | Ploetz |
| 5,941,832 A | 8/1999 | Tumey et al. |
| 5,970,118 A | 10/1999 | Sokolov |
| 5,986,662 A | 11/1999 | Argiro et al. |
| 5,999,836 A | 12/1999 | Nelson et al. |
| 6,005,907 A | 12/1999 | Ploetz |
| 6,022,325 A | 2/2000 | Siczek et al. |
| 6,075,879 A | 6/2000 | Roehrig et al. |
| 6,091,841 A | 7/2000 | Rogers et al. |
| 6,101,236 A | 8/2000 | Wang et al. |
| 6,137,527 A | 10/2000 | Abdel-Malek et al. |
| 6,141,398 A | 10/2000 | He et al. |
| 6,149,301 A | 11/2000 | Kautzer et al. |
| 6,175,117 B1 | 1/2001 | Komardin et al. |
| 6,196,715 B1 | 3/2001 | Nambu et al. |
| 6,216,540 B1 | 4/2001 | Nelson et al. |
| 6,219,059 B1 | 4/2001 | Argiro |
| 6,233,473 B1 | 5/2001 | Shepherd et al. |
| 6,243,441 B1 | 6/2001 | Zur |
| 6,256,370 B1 | 7/2001 | Yavuz |
| 6,272,207 B1 | 8/2001 | Tang |
| 6,289,235 B1 | 9/2001 | Webber et al. |
| 6,292,530 B1 | 9/2001 | Yavus et al. |
| 6,293,282 B1 | 9/2001 | Lemelson |
| 6,327,336 B1 | 12/2001 | Gingold et al. |
| 6,341,156 B1 | 1/2002 | Baetz et al. |
| 6,375,352 B1 | 4/2002 | Hewes et al. |
| 6,411,836 B1 | 6/2002 | Patel et al. |
| 6,415,015 B2 | 7/2002 | Nicolas et al. |
| 6,442,288 B1 | 8/2002 | Haerer et al. |
| 6,459,925 B1 | 10/2002 | Nields et al. |
| 6,501,819 B2 | 12/2002 | Unger et al. |
| 6,556,655 B1 | 4/2003 | Chichereau et al. |
| 6,574,304 B1 | 6/2003 | Hsieh et al. |
| 6,597,762 B1 | 7/2003 | Ferrant et al. |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes et al. |
| 6,638,235 B2 | 10/2003 | Miller et al. |
| 6,647,092 B2 | 11/2003 | Eberhard et al. |
| 6,744,848 B2 | 6/2004 | Stanton et al. |
| 6,748,044 B2 | 6/2004 | Sabol et al. |
| 6,751,285 B2 | 6/2004 | Eberhard et al. |
| 6,758,824 B1 | 7/2004 | Miller et al. |
| 6,813,334 B2 | 11/2004 | Koppe et al. |
| 6,882,700 B2 | 4/2005 | Wang et al. |
| 6,885,724 B2 | 4/2005 | Li et al. |
| 6,909,792 B1 | 6/2005 | Carrott et al. |
| 6,912,319 B1 | 6/2005 | Barnes et al. |
| 6,940,943 B2 | 9/2005 | Claus et al. |
| 6,970,531 B2 | 11/2005 | Eberhard et al. |
| 6,978,040 B2 | 12/2005 | Berestov |
| 6,987,831 B2 | 1/2006 | Ning |
| 6,999,554 B2 | 2/2006 | Mertelmeier |
| 7,110,490 B2 | 9/2006 | Eberhard et al. |
| 7,110,502 B2 | 9/2006 | Tsuji |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,245,694 B2 | 7/2007 | Jing et al. |
| 7,302,031 B2 | 11/2007 | Hjarn et al. |
| 7,315,607 B2 | 1/2008 | Ramsauer |
| 7,319,735 B2 | 1/2008 | Defreitas et al. |
| 7,323,692 B2 | 1/2008 | Rowlands et al. |
| 7,430,272 B2 | 9/2008 | Jing et al. |
| 7,443,949 B2 | 10/2008 | Defreitas et al. |
| 7,466,795 B2 | 12/2008 | Eberhard et al. |
| 7,577,282 B2 | 8/2009 | Gkanatsios et al. |
| 7,583,786 B2 | 9/2009 | Jing et al. |
| 7,609,806 B2 | 10/2009 | Defreitas et al. |
| 7,616,801 B2 | 11/2009 | Gkanatsios et al. |
| 7,630,533 B2 | 12/2009 | Ruth et al. |
| 7,688,940 B2 | 3/2010 | Defreitas et al. |
| 7,697,660 B2 | 4/2010 | Ning |
| 7,702,142 B2 | 4/2010 | Ren et al. |
| 7,760,853 B2 | 7/2010 | Jing et al. |
| 7,760,924 B2 | 7/2010 | Ruth et al. |
| 7,792,245 B2 | 9/2010 | Hitzke et al. |
| 7,831,296 B2 | 11/2010 | DeFreitas et al. |
| 7,869,563 B2 * | 1/2011 | Defreitas et al. ............ 378/37 |
| 7,881,428 B2 | 2/2011 | Jing et al. |
| 7,916,915 B2 | 3/2011 | Gkanatsios et al. |
| 7,949,091 B2 | 5/2011 | Jing et al. |
| 7,986,765 B2 | 7/2011 | Defreitas et al. |
| 7,991,106 B2 | 8/2011 | Ren et al. |

(56) References Cited

U.S. PATENT DOCUMENTS

| | | | |
|---|---|---|---|
| 8,131,049 B2 | 3/2012 | Ruth et al. | |
| 8,155,421 B2 | 4/2012 | Ren et al. | |
| 8,170,320 B2 | 5/2012 | Smith et al. | |
| 8,175,219 B2 * | 5/2012 | Defreitas et al. | 378/37 |
| 8,285,020 B2 | 10/2012 | Gkanatsios et al. | |
| 8,416,915 B2 | 4/2013 | Jing et al. | |
| 8,452,379 B2 | 5/2013 | DeFreitas et al. | |
| 8,532,745 B2 | 9/2013 | DeFreitas et al. | |
| 8,559,595 B2 | 10/2013 | Defreitas et al. | |
| 8,565,372 B2 | 10/2013 | Stein et al. | |
| 8,565,374 B2 | 10/2013 | DeFreitas et al. | |
| 8,571,289 B2 | 10/2013 | Ruth et al. | |
| 8,712,127 B2 | 4/2014 | Ren et al. | |
| 8,831,171 B2 | 9/2014 | Jing et al. | |
| 2001/0038681 A1 | 11/2001 | Stanton et al. | |
| 2002/0012450 A1 | 1/2002 | Tsujii | |
| 2002/0050986 A1 | 5/2002 | Inouc et al. | |
| 2002/0075997 A1 | 6/2002 | Unger et al. | |
| 2002/0113681 A1 | 8/2002 | Byram | |
| 2003/0018272 A1 | 1/2003 | Treado et al. | |
| 2003/0026386 A1 | 2/2003 | Tang et al. | |
| 2003/0072417 A1 | 4/2003 | Kaufhold et al. | |
| 2003/0073895 A1 | 4/2003 | Nields et al. | |
| 2003/0095624 A1 | 5/2003 | Eberhard et al. | |
| 2003/0169847 A1 | 9/2003 | Karellas et al. | |
| 2003/0194050 A1 | 10/2003 | Eberhard | |
| 2003/0194051 A1 | 10/2003 | Wang et al. | |
| 2003/0194121 A1 | 10/2003 | Eberhard et al. | |
| 2003/0210254 A1 | 11/2003 | Doan et al. | |
| 2003/0212327 A1 | 11/2003 | Wang et al. | |
| 2003/0215120 A1 | 11/2003 | Uppaluri et al. | |
| 2004/0008809 A1 | 1/2004 | Webber | |
| 2004/0066882 A1 | 4/2004 | Eberhard et al. | |
| 2004/0066884 A1 | 4/2004 | Hermann Claus et al. | |
| 2004/0066904 A1 | 4/2004 | Eberhard et al. | |
| 2004/0070582 A1 | 4/2004 | Smith et al. | |
| 2004/0094167 A1 | 5/2004 | Brady et al. | |
| 2004/0101095 A1 | 5/2004 | Jing et al. | |
| 2004/0109529 A1 * | 6/2004 | Eberhard et al. | 378/23 |
| 2004/0171986 A1 | 9/2004 | Tremaglio, Jr. et al. | |
| 2004/0267157 A1 | 12/2004 | Miller et al. | |
| 2005/0049521 A1 | 3/2005 | Miller et al. | |
| 2005/0063509 A1 | 3/2005 | DeFreitas et al. | |
| 2005/0078797 A1 | 4/2005 | Danielsson et al. | |
| 2005/0089205 A1 | 4/2005 | Kapur | |
| 2005/0105679 A1 | 5/2005 | Wu et al. | |
| 2005/0113681 A1 | 5/2005 | DeFreitas et al. | |
| 2005/0113715 A1 | 5/2005 | Schwindt et al. | |
| 2005/0129172 A1 * | 6/2005 | Mertelmeier | 378/37 |
| 2005/0135555 A1 | 6/2005 | Claus et al. | |
| 2005/0135664 A1 | 6/2005 | Kaufhold et al. | |
| 2005/0226375 A1 | 10/2005 | Eberhard et al. | |
| 2006/0009693 A1 | 1/2006 | Hanover et al. | |
| 2006/0030784 A1 | 2/2006 | Miller et al. | |
| 2006/0074288 A1 | 4/2006 | Kelly | |
| 2006/0098855 A1 | 5/2006 | Gkanatsios et al. | |
| 2006/0129062 A1 | 6/2006 | Nicoson et al. | |
| 2006/0155209 A1 | 7/2006 | Miller et al. | |
| 2006/0257009 A1 | 11/2006 | Wang | |
| 2006/0269041 A1 | 11/2006 | Mertelmeier | |
| 2006/0291618 A1 | 12/2006 | Eberhard et al. | |
| 2007/0030949 A1 | 2/2007 | Jing et al. | |
| 2007/0036265 A1 | 2/2007 | Jing et al. | |
| 2007/0076844 A1 | 4/2007 | Defreitas et al. | |
| 2007/0140419 A1 | 6/2007 | Souchay | |
| 2007/0223651 A1 | 9/2007 | Wagenaar et al. | |
| 2007/0225600 A1 | 9/2007 | Weibrecht et al. | |
| 2007/0242800 A1 | 10/2007 | Jing et al. | |
| 2008/0019581 A1 | 1/2008 | Gkanatsios et al. | |
| 2008/0045833 A1 | 2/2008 | DeFreitas et al. | |
| 2008/0101537 A1 | 5/2008 | Sendai | |
| 2008/0112534 A1 | 5/2008 | Defreitas | |
| 2008/0130979 A1 | 6/2008 | Ren | |
| 2008/0198966 A1 | 8/2008 | Hjam | |
| 2009/0003519 A1 | 1/2009 | Defreitas et al. | |
| 2009/0010384 A1 | 1/2009 | Jing et al. | |
| 2009/0080594 A1 | 3/2009 | Brooks et al. | |
| 2009/0080602 A1 | 3/2009 | Brooks et al. | |
| 2009/0080604 A1 | 3/2009 | Shores et al. | |
| 2009/0135997 A1 | 5/2009 | Defreitas et al. | |
| 2009/0141859 A1 | 6/2009 | Gkanatsios et al. | |
| 2009/0143674 A1 | 6/2009 | Nields et al. | |
| 2009/0213987 A1 | 8/2009 | Stein et al. | |
| 2009/0238424 A1 | 9/2009 | Arakita et al. | |
| 2009/0268865 A1 | 10/2009 | Ren et al. | |
| 2009/0296882 A1 | 12/2009 | Gkanatsios | |
| 2009/0304147 A1 | 12/2009 | Jing et al. | |
| 2010/0034450 A1 | 2/2010 | Mertelmeier | |
| 2010/0054400 A1 | 3/2010 | Ren | |
| 2010/0086188 A1 | 4/2010 | Ruth | |
| 2010/0150306 A1 | 6/2010 | Defreitas et al. | |
| 2010/0195882 A1 | 8/2010 | Ren | |
| 2010/0226475 A1 | 9/2010 | Smith | |
| 2010/0290585 A1 | 11/2010 | Eliasson | |
| 2011/0069809 A1 | 3/2011 | Defreitas et al. | |
| 2011/0087132 A1 | 4/2011 | DeFreitas et al. | |
| 2011/0178389 A1 | 7/2011 | Kumar et al. | |
| 2011/0234630 A1 | 9/2011 | Batman et al. | |
| 2011/0237927 A1 | 9/2011 | Brooks et al. | |
| 2013/0028374 A1 | 1/2013 | Gkanatsios et al. | |
| 2014/0044230 A1 | 2/2014 | Stein et al. | |
| 2014/0086471 A1 | 3/2014 | Ruth et al. | |
| 2014/0098935 A1 | 4/2014 | Defreitas et al. | |
| 2014/0232752 A1 | 8/2014 | Ren et al. | |

FOREIGN PATENT DOCUMENTS

| | | |
|---|---|---|
| EP | 1428473 | 6/2004 |
| EP | 1759637 | 3/2007 |
| EP | 2236085 | 6/2010 |
| EP | 1569556 | 4/2012 |
| EP | 1986548 | 1/2013 |
| EP | 2602743 | 11/2014 |
| JP | 2006-231054 | 9/2006 |
| JP | 2007-50264 | 3/2007 |
| JP | 2007-521911 | 8/2007 |
| JP | 2008-67933 | 3/2008 |
| WO | WO 90/05485 | 5/1990 |
| WO | WO 90/05495 | 5/1990 |
| WO | WO 93/17620 | 9/1993 |
| WO | WO 94/06352 | 3/1994 |
| WO | WO 97/00649 | 9/1997 |
| WO | WO 98/16903 | 4/1998 |
| WO | WO 00/51484 | 9/2000 |
| WO | WO 03/020114 | 3/2003 |
| WO | WO 03/057564 | 7/2003 |
| WO | WO 2004/043535 | 5/2004 |
| WO | WO 2005/051197 | 6/2005 |
| WO | WO 2005/110230 | 11/2005 |
| WO | WO 2005/112767 | 12/2005 |
| WO | WO 2006/055830 | 5/2006 |
| WO | WO 2006/058160 | 6/2006 |
| WO | WO 2008/014670 | 2/2008 |
| WO | WO 2008/054436 | 5/2008 |

OTHER PUBLICATIONS

"Essentials for life: Senographe Essential Full-Field Digital Mammography system", GE Health-care Brochure, MM-0132-05.06-EN-US, 2006, 12 pgs.

"Filtered Back Projection," (NYGREN) published May 8, 2007; URL:http://web.archive.org/web/19991010131715/http://www.owlnet.rice.edu/-.about.elec539/Projects97/cult/node2.html., 2 pgs.

"Lorad Selenia" Document B-BI-SEO US/Intl (May 2006) copyright Hologic 2006, 12 pgs.

Aslund, Magnus, "Digital Mammography with a Photon Counting Detector in a Scanned Multislit Geometry", Doctoral Thesis, Dept of Physics, Royal Institute of Technology, Stockholm, Sweden, Apr. 2007, 51 pages.

Chan, Heang-Ping et al., "ROC study of the effect of stereoscopic imaging on assessment of breast lesions", Medical Physics, vol. 32, No. 4, Apr. 2005, 7 pgs.

(56) References Cited

OTHER PUBLICATIONS

Cole, Elodia, et al., "The Effects of Gray Scale Image Processing on Digital Mammography Interpretation Performance", Academic Radiology, vol. 12, No. 5, pp. 585-595, May 2005.

Digital Clinical Reports, Tomosynthesis, GE Brochure 98-5493, Nov. 1998, 8 pgs.

Dobbins, James T., "Digital x-ray tomosynthesis: current state of the art and clinical potential," Physics in Medicine and Biology, Taylor and Francis LTD, London GB, vol. 48, No. 19, Oct. 7, 2003, 42 pages.

Federica Pediconi et al., "Color-coded automated signal intensity-curve for detection and characterization of breast lesions: Preliminary evaluation of a new software for MR-based breast imaging", International Congress Series 1281 (2005) 1081-1086.

Grant, David G., "Tomosynthesis: a three-dimensional imaging technique", IEEE Trans. Biomed. Engineering, vol. BME-19, #1, Jan. 1972, pp. 20-28.

Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.

Mammographic Accreditation Phantom, http://www.cirsinc.com/pdfs/015cp.pdf. (2006), 2 pgs.

Senographe 700 & 800T (GE); 2-page download on Jun. 22, 2006 from www.gehealthcare.com/inen/rad/whe/products/mswh800t.html.; Figures 1-7 on 4 sheets re lateral shift compression paddle, 2 pgs.

Smith, A., "Fundamentals of Breast Tomosynthesis", White Paper, Hologic Inc., WP-00007, Jun. 2008, 8 pgs.

Wheeler F. W., et al. "Micro-Calcification Detection in Digital Tomosynthesis Mammography" Proceedings of SPIE, Conf-Physics of Semiconductor Devices, Dec. 11, 2001 to Dec. 15, 2001, Delhi, SPIE, US, vol. 6144, Feb. 13, 2006, 12 pgs.

Wu, Tao, et al. "Tomographic Mammography Using a Limited Number of Low-Dose Cone-Beam Projection Images" Medical Physics, AIP, Melville, NY, vol. 30, No. 3, Mar. 1, 2003, p. 365-380.

* cited by examiner

INTEGRATED MULTI-MODE MAMMOGRAPHY/TOMOSYNTHESIS X-RAY SYSTEM AND METHOD

RELATED APPLICATION

This application is a continuation application and claims priority under 35 USC §120 to U.S. patent application Ser. No. 13/462,342 filed May 2, 2012, which is a continuation of U.S. Pat. No. 8,175,219 filed Nov. 29, 2010, which is a continuation of U.S. Pat. No. 7,869,563, filed Feb. 22, 2008, which is a national stage entry of PCT/US2005/042613, filed Nov. 23, 2005. Each of the above is incorporated by reference.

FIELD OF THE INVENTION

This patent specification pertains to x-ray mammography and, more specifically, to an integrated system for selectively carrying out x-ray mammography and/or tomosynthesis imaging and a method of using such a system.

BACKGROUND OF THE INVENTION

X-ray mammography has long been a screening modality for breast cancer and other lesions, and also has been relied on for diagnostic and other purposes. For many years, the breast image was recorded on x-ray film but more recently digital x-ray image receptors have come into use, as in the Selenia™ mammography system available from Hologic, Inc. of Bedford, Mass. and its division Lorad Corporation of Danbury, Conn. For mammograms, a cone-shaped or pyramid-shaped x-ray beam passes through the compressed breast and forms a two-dimensional projection image. Any one of a number of orientation can be used, such as cranial-caudal (CC) or MLO (mediolateral-oblique) orientation. More recently, breast x-ray tomosynthesis has been proposed. The technology typically involves taking two-dimensional (2D) projection images of the immobilized breast at each of a number of angles of the x-ray beam relative to the breast and processing the resulting x-ray measurements to reconstruct images of breast slices that typically are in planes transverse to the x-ray beam axis, such as parallel to the image plane of a mammogram of the same breast. The range of angles is substantially less than in computerized tomography, i.e., substantially less than 180°, e.g. ±15°. Tomosynthesis technology is described in U.S. patent application Ser. No. 10/723,486 filed Nov. 26, 2003; a prototype of a unit with at least some of the described features was shown at the 2003 Radiological Society of North America meeting in Chicago, Ill. Additional prototypes are in clinical testing in this country as of the filing of this patent specification. Other approaches to tomosynthesis also have been proposed; see, e.g., U.S. Pat. Nos. 4,496,557, 5,051,904, 5,359,637, 6,289,235, and 6,647,092, published U.S. Patent Applications Nos. 2001/0038861, 2004/0668V, 2004/0066884, and 2004/0066904, and Digital Clinical Reports, Tomosynthesis (GE Brochure 98-5493, 11/98). How to reconstruct tomosynthesis images is discussed in DG Grant, "Tomosynthesis: a three-dimensional imaging technique", IEEE Trans. Biomed, Engineering, Vol BME-19, #1, (January 1972), pp 20-28. See, also, U.S. Provisional Application Ser. No. 60/628,516, filed Nov. 15, 2004, and entitled "Matching geometry generation and display of mammograms and tomosynthesis images". Mammography systems can also be used in interventional procedures, such as biopsy, by adding a biopsy station (for example, the StereoLoc II™ Upright Stereotactic Breast Biopsy System, which is available from Hologic, Inc.). The patents, applications, brochures, and article cited above are hereby incorporated by reference in this patent specification as though fully set forth herein.

In clinical use, it can be desirable for a number of reasons to assess both tomosynthesis images and conventional mammograms of the patient's breasts. For example, the decades of conventional mammograms have enabled medical professionals to develop valuable interpretation expertise. Mammograms may offer good visualization of microcalcifications, and can offer higher spatial resolution compared with tomosynthesis. Tomosynthesis images may have different desirable characteristics—e.g., they may offer better visualization of structures that can be obscured by overlying or underlying tissue in a conventional mammogram.

While the existing and proposed systems for x-ray mammography and tomosynthesis offer many advantages, it is believed that a need still exists for further improvements to make mammography/tomosynthesis more useful, and that it is particularly desirable to make it possible to use the same system in different modes of operation and thereby reduce acquisition and operating costs and provide greater clinical value and convenience.

SUMMARY

This patent specification describes examples of systems and methods for multi-mode breast x-ray imaging. A single system carries out breast imaging in modes that include standard mammography, diagnostic mammography, dynamic imaging such as with a contrast agent and at different x-ray energies, tomosynthesis imaging, combined standard and tomosynthesis imaging during a single breast compression, needle localization, and stereotactic imaging with a biopsy station mounted to the system.

In an example of a system using the teachings of this patent specification, a compression arm assembly for compressing and immobilizing the breast for x-ray imaging, an x-ray tube assembly, and an x-ray image receptor can be angled relative to each other for different imaging protocols and modes. They can be independently rotated and synchronized as needed, or can be mechanically linked for appropriate synchronized rotation. A patient shield can be mounted to the compression arm assembly to provide a mechanical interlock against patient contact with the rotating x-ray tube assembly. A fully retractable anti-scatter grid can be used that can cover the imaging area of the x-ray receptor in some modes but be retracted completely outside the imaging area for other modes.

The exemplary system further includes a breast compression paddle that is laterally movable, under manual control or when motorized and operating under software control. The compression paddle can shift automatically depending on the view to be acquired. For example, the paddle can be centered on the x-ray receptor for a CC view, shifted to one lateral side of the receptor for an MLO view of one breast and to the other lateral side of the receptor for an MLO view of the other breast. The paddle can be automatically recognized by the system when mounted so that the shifts can be adjusted to the type of paddle.

The compression paddle can be easily removable from a support that has a mechanism for laterally moving the paddle and for allowing the paddle to tilt for better conformance with the breast for selected image modes but locking the paddle against tilt for other modes. With the movement mechanism in the support and not integral with the paddle, the paddle can be simple and inexpensive, and easy to mount to and remove from the support. A number of relatively inexpensive paddles of different sizes and shapes can be provided and conveniently interchanged to suit different procedures and patients.

DETAILED DESCRIPTION OF PREFERRED EMBODIMENTS

Figure 1:
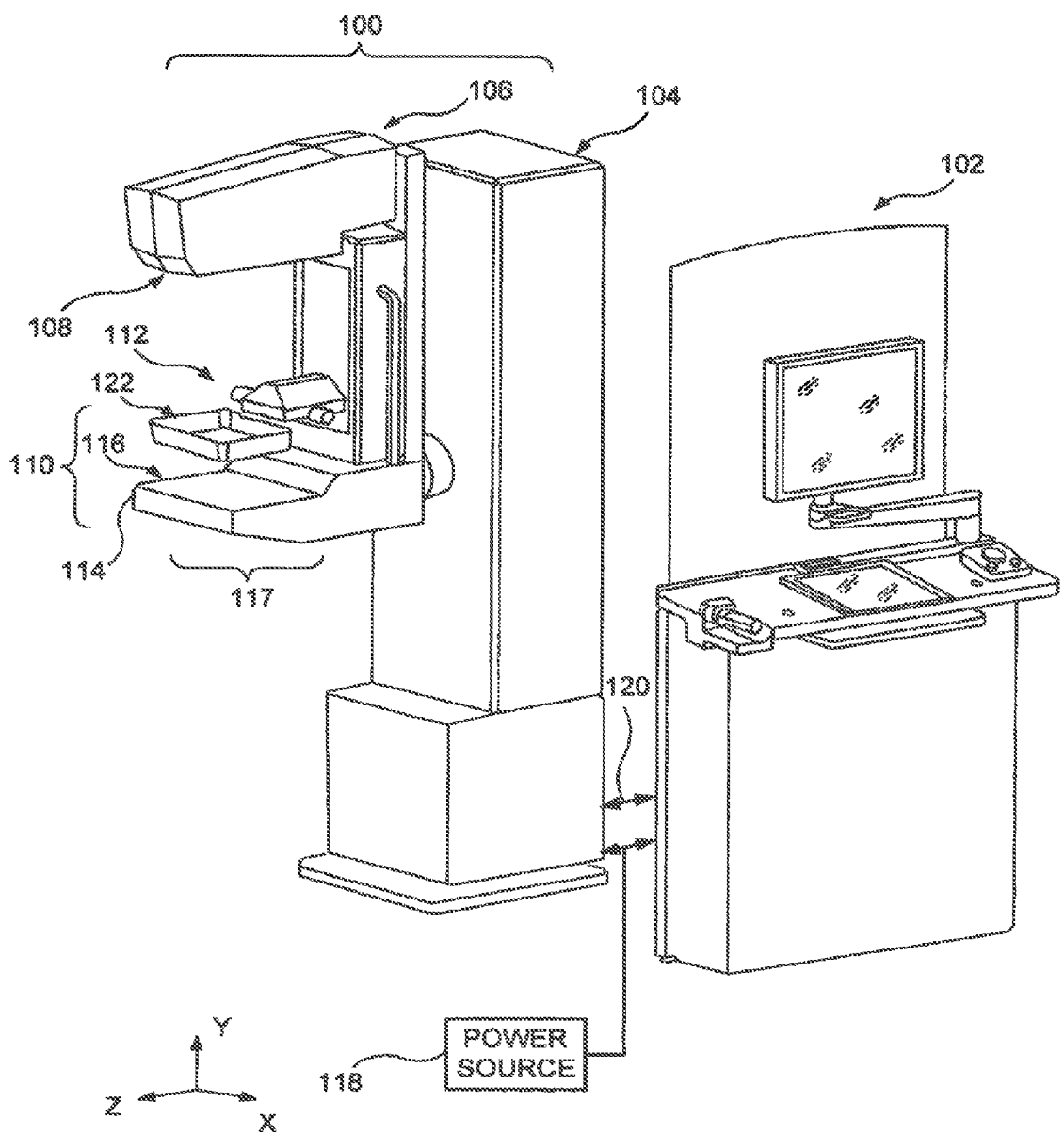
FIG. 1 is a perspective view of a gantry and an acquisition workstation in accordance with an example of the disclosed system.

In describing examples and preferred embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

FIGS. 1-6 illustrate a non-limiting example of a multi-mode mammography/tomosynthesis system comprising a gantry 100 and a data acquisition work-station 102. Gantry 100 includes a housing 104 supporting a tube arm assembly 106 rotatably mounted thereon to pivot about a horizontal axis 402 (FIG. 4) and carrying an x-ray tube assembly 108. X-ray tube assembly 108 includes (1) an x-ray tube generating x-ray energy in a selected range, such as 20-50 kV, at mAs such as in the range 3-400 mAs, with focal spots such as a nominal size 0.3 mm large spot and nominal size 0.1 mm small spot (2) supports for multiple filters such as molybdenum, rhodium, aluminum, copper, and tin Ethers, and (3) an adjustable collimation assembly selectively collimating the x-ray beam from the focal spot in a range such as from 7×8 cm to 24×29 when measured at the image plane of an x-ray image receptor included in the system, at a maximum source-image distance such as 75 cm. Also mounted on housing 104, for rotation about the same axis 402, is a compression arm assembly 110 that comprises a compression plate 122 and a receptor housing 114 having an upper surface 116 serving as a breast plate and enclosing a detector subsystem system 117 comprising a flat panel x-ray receptor 502 (FIG. 5), a retractable anti-scatter grid 504 and a mechanism 506 for driving and retracting anti-scatter grid 504. Housing 104 also encloses the following components schematically illustrated in FIG. 4: a vertical travel assembly 404 for moving tube arm assembly 106 and compression arm assembly 110 up and down to accommodate a particular patient or imaging position, a tube arm assembly rotation mechanism 406 to rotate tube arm assembly 106 about axis 402 for different imaging positions, a detector subsystem rotation mechanism 408 for rotating components of detector subsystem 117 (such as x-ray receptor 502) about axis 402 to accommodate different operations modes, and couple/uncouple mechanism 410 to selectively couple or uncouple tube arm assembly 106 and compression arm assembly 110 to and from each other, and tube arm assembly 106 and detector subsystem 117 to and from each other. Housing 104 also encloses suitable motors and electrical and mechanical components and connections to implement the functions discussed here. A patient shield 200, schematically illustrated in FIG. 2, can be secured to compression arm assembly 110 to provide a mechanical interlock against patient contact with the rotating x-ray tube arm assembly 106. Workstation 102 comprises components similar to those in the Selenia™ mammography system, including a display screen (typically a flat panel display that may include touch-screen functionality), user interface devices such as a keyboard, possibly a touch-screen, and a mouse or trackball, and various switches and indicator lights and/or displays. Workstation 102 also includes computer facilities similar to those of the Selenia™ system (but adapted through hardware, firmware and software differences) for controlling gantry 100 and for processing, storing and displaying data received from gantry 100. A power generation facility for x-ray tube assembly 108 may be included in housing 104 or in work-station 102. A power source 118 powers work-station 102. Gantry 100 and work-station 102 exchange data and controls over a schematically illustrated connection 120.

Figure 6:
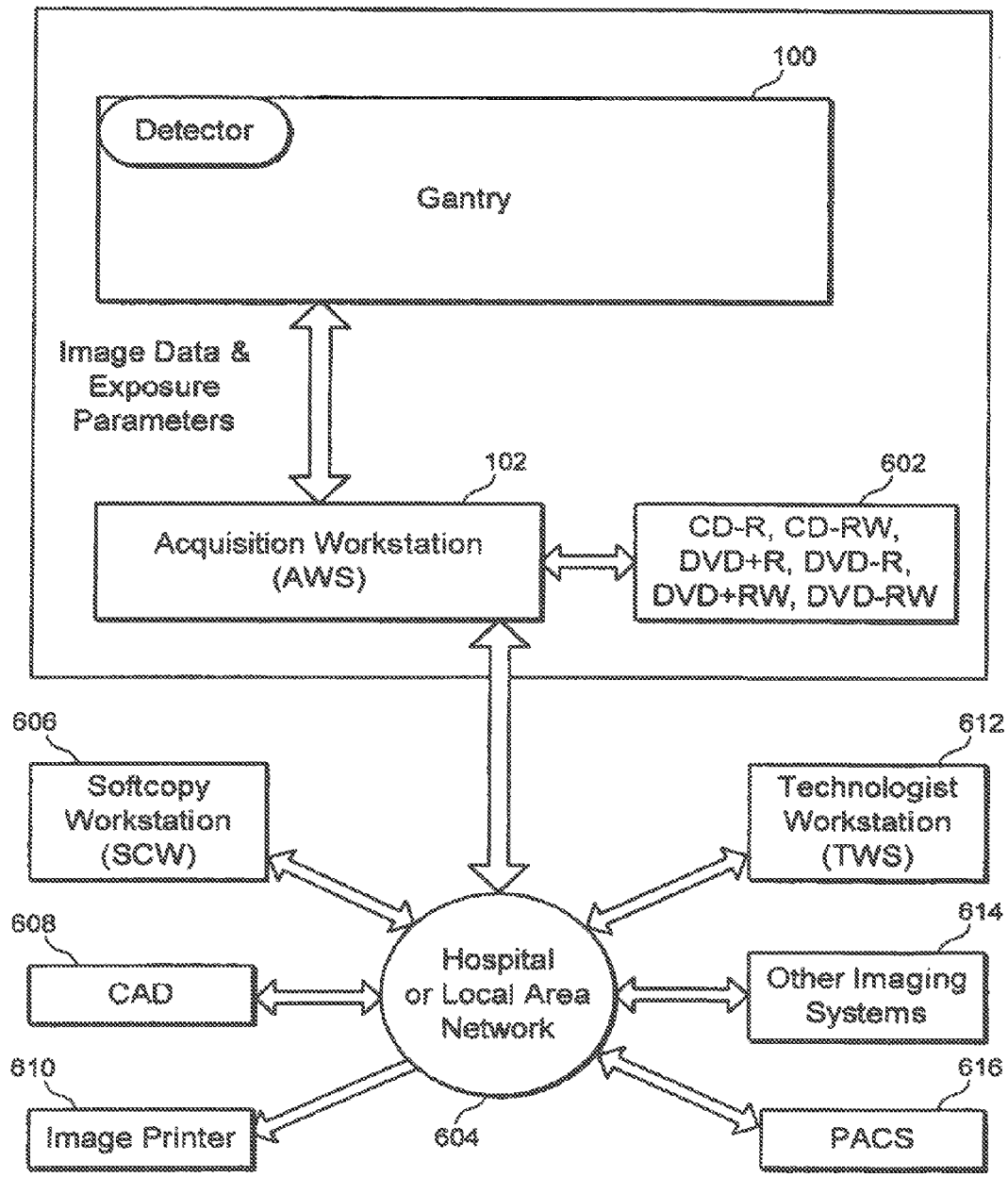
FIG. 6 is a block diagram of the disclosed system when connected to other systems.

As illustrated in FIG. 6, additional storage facilities 602 can be connected to work-station 102, such as one or more optical disc drives for storing information such as images and/or for providing is to work-station 102 such as previously obtained images and software, or a local printer (not shown). In addition, the disclosed system can be connected to a hospital or local area or other network 604, and through the network to other systems such as a soft copy workstation 606, a CAD (Computer Aided Detection) station 608 for computer-processing mammography and/or tomosynthesis images to identify likely abnormalities, an image printer 610 for printing images, a technologist workstation 612, other imaging systems 614 such as other mammography systems or systems for other modalities for exchange of images and/or other information, and to a PACS (Picture Archiving) systems 616 for archiving images and other information and/or retrieving images and other information.

Figure 7:
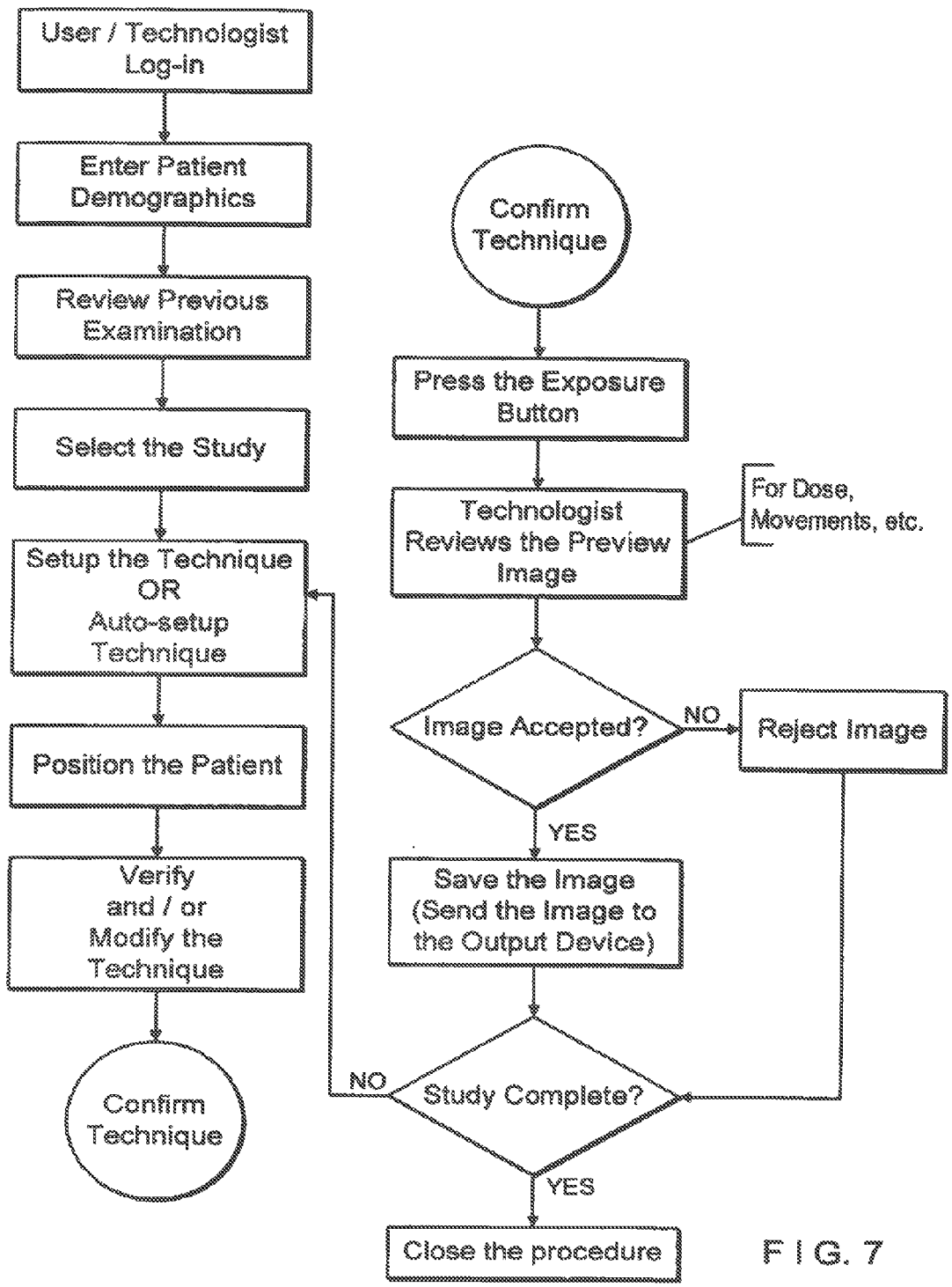
FIG. 7 is a flow chart illustrating a general work flow for the disclosed system.

The illustrated system has several modes of operation. An example of typical workflow generally applicable for each mode is illustrated in FIG. 7, and several examples of operational modes are discussed below. Of course, this is only one example and workflow steps may be arranged differently. In all modes, the operator can perform x-ray exposure using manual setting of technic factors such as mA and mSec, or can use an automatic exposure control as known in the art to set the exposure time, kV and filter modes for an image, for example by using a short, low x-ray dose pre-exposure. Workstation 102 is set up to record the exposure technic information and associate it with the breast image for later review.

Figure 8:
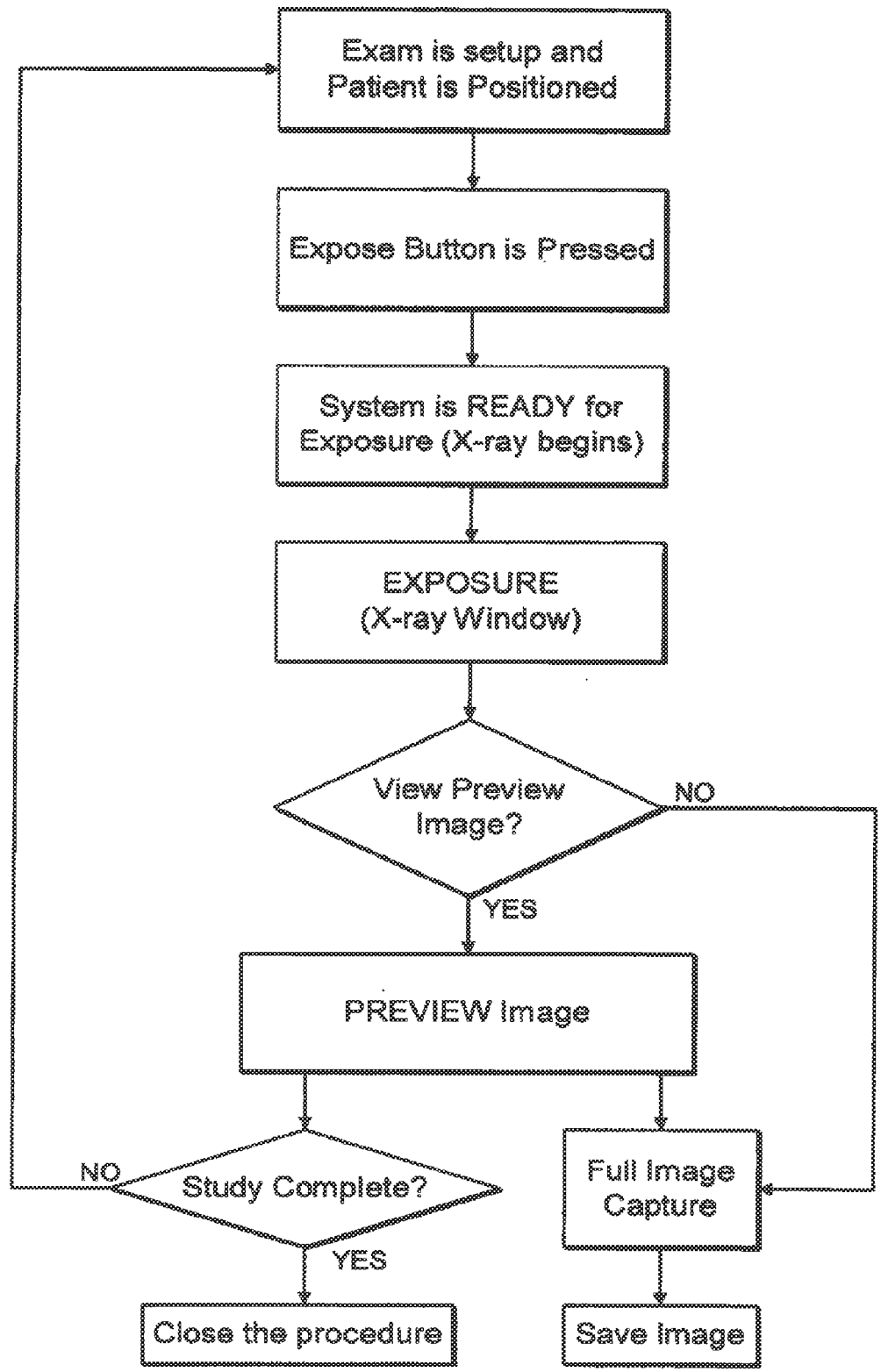
FIG. 8 is a flow chart illustrating one of several examples of work flow for a standard mammography mode.
Figure 9:
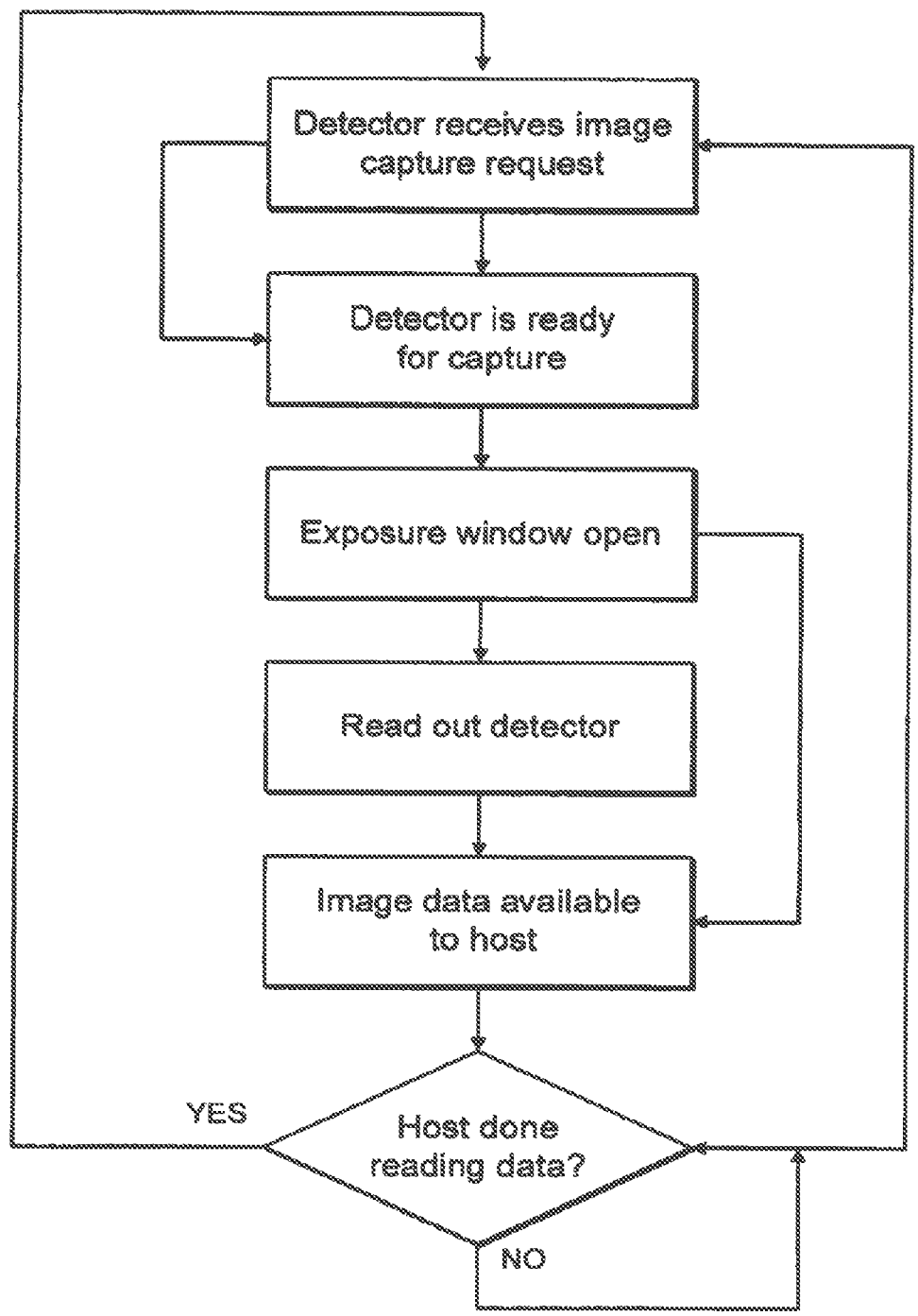
FIG. 9 is a flow chart illustrating one of several examples of work flow for an image detector subsystem in the standard mammography mode.
Figure 10:
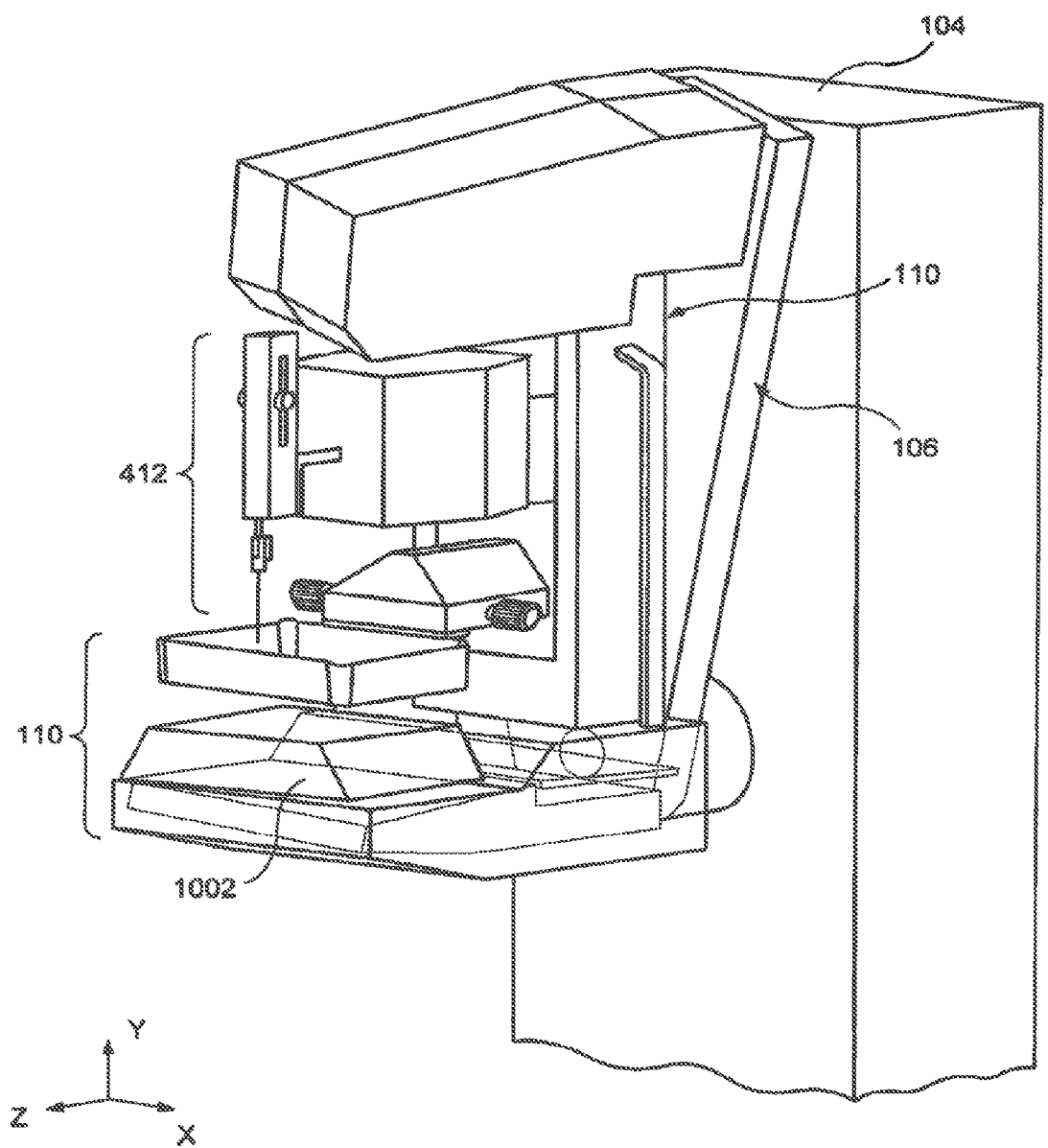
FIG. 10 is a perspective view of the structure of FIG. 4.

In standard mammography mode, typically used for screening mammography, tube arm assembly 106 and compression arm assembly 110 are coupled and locked together by 410 in a relative position such as seen in FIG. 1, such that an x-ray beam from x-ray tube assembly 108 illuminates x-ray receptor 502 when the patient's breast is compressed by compression device 112. In this mode, the system operates in a manner similar to said Selenia™ system to take a mammogram. Vertical travel assembly 404 and tube arm rotation mechanism 406 can make vertical adjustments to accommodate a patient, and can rotate tube arm assembly 106 and compression arm assembly 110 together as a unit about axis 402 for different image orientations such as for CC and for MLO images. For example, tube arm assembly 106 and compression an assembly 110 can rotate between (−195°) and (+150°) about axis 402. As in the Selenia™ system, compression device 112 includes a compression paddle 122 that can move laterally, in a direction along the chest wall of a patient, to adjust for different imaging orientations. However, as described further below, the mechanism for supporting and moving compression paddle 122 is different. Typically, anti-scatter grid 504 is over x-ray receptor 502 in the standard mammography mode to reduce the effect of x-ray scatter. FIG. 8 illustrates a typical workflow for an exposure in standard mammography mode, and FIG. 10 illustrates an example of the operation of detector subsystem 117 in standard mammography. Of course, these are only examples; other workflows steps or orders of steps can be used instead.

In a diagnostic mode, the patient's breast can be spaced from upper surface 116, for example by an x-ray translucent spacer gantry 1002 (FIG. 10), with the system otherwise similar to FIG. 1, for a magnification of up to 1.8, for example. In this mode, as in standard mammography, tube arm assembly 106 and compression arm assembly 110 are locked to each other and can move up or down and rotate about axis 402 for different image orientation. A different spacer 1002 can be used for a different degree of magnification. Also, differently shaped or dimensioned compression paddles 122 can be used for different breast compression effects. The x-ray tube in x-ray tube assembly 108 can be set to a smaller focal spot size to improve a diagnostic image. In this mode, anti-scatter grid 504 typically is retracted when magnification is used such that grid 504 is completely out of the image. The user can elect not to use a spacer 1002 in diagnostic imaging, in which case anti-scatter grid 504 can be used over the entire image.

In a dynamic imaging mode, a number of breast images are taken while the patient's breast remains compressed. In one technique, an agent such as iodine is injected into the patient and after a suitable waiting time such as about one minute for a maximum uptake, two images breast are taken in rapid succession, for example one at an x-ray energy just above the K-edge of iodine and one at an energy just below the K-edge. Alternatively, a succession of breast images can be taken at a single x-ray energy band or bands jug above and below the K-edge, or at another x-ray energy range, to track the uptake of agent over time. Another technique adds taking a baseline breast image before or soon after injecting the agent and using it together with later breast images to generate subtraction images that provide better visualization of anatomy that may be of interest. Still another dynamic imaging mode technique comprises injecting a contrast agent and taking a succession of images over a period such as 5-7 minutes, for example one image every minute, and processing the image data to generate for each pixel, or at least for each pixel of interest, a histogram of the change in the pixel value, to thereby use the manner in which pixel values change to differential abnormal tissue. For this mode, work-station 102 can store preset data that commands gantry 100 and work-station 102 to take a desired sequence of images for the dynamic mode technique selected by the operator, such that the command data sets the appropriate parameters such as x-ray energy, dose, timing of images, etc. Alternatively, such processing to assess changes in pixel values can be done for a region of interest rather than over individual pixels, to produce information such as a measure of changes in the average pixel values in the region of interest.

Figure 2:
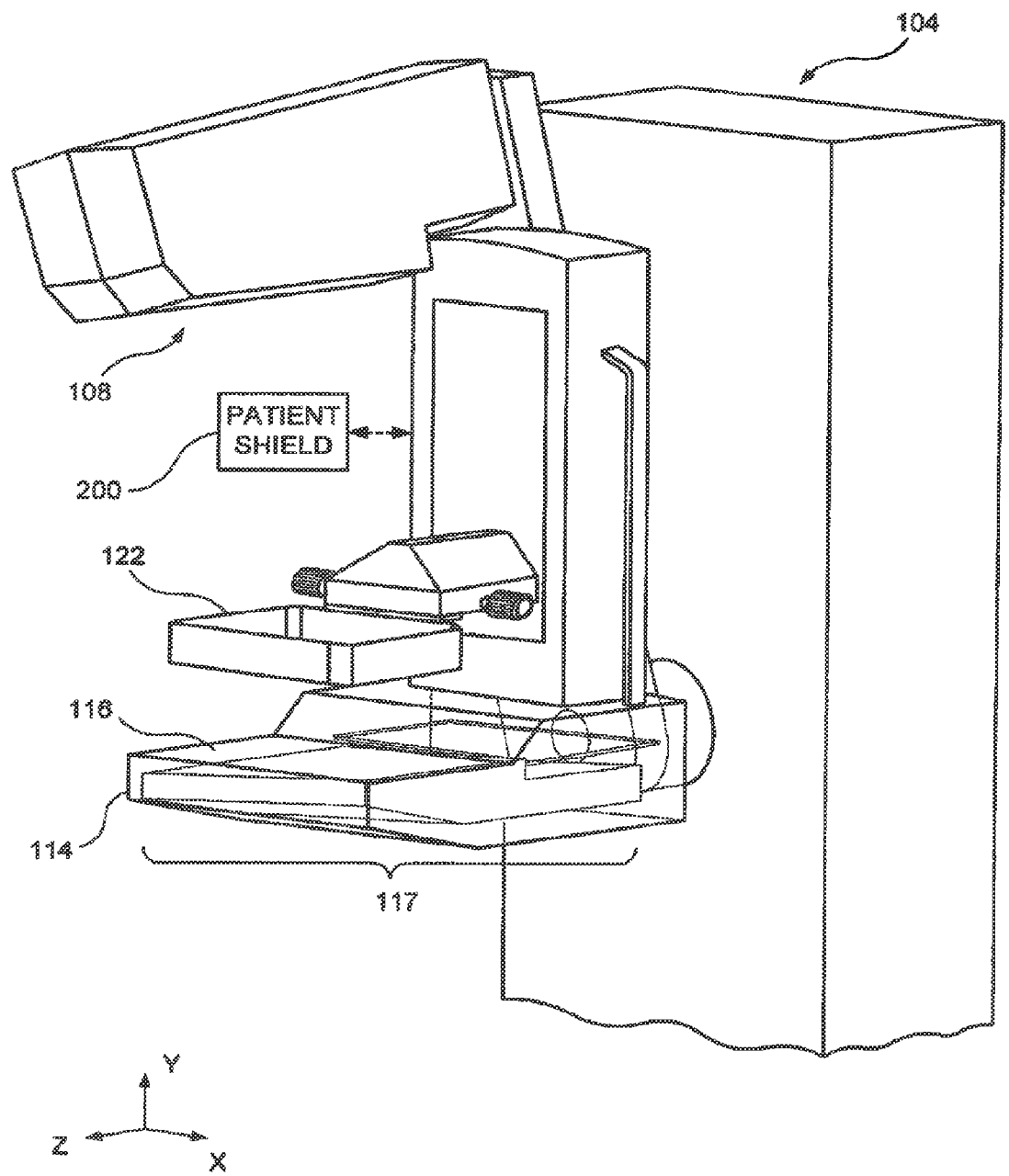
FIG. 2 is an enlarged view of a portion of the system of FIG. 1, with a tube arm assembly in a rotated position.
Figure 3:
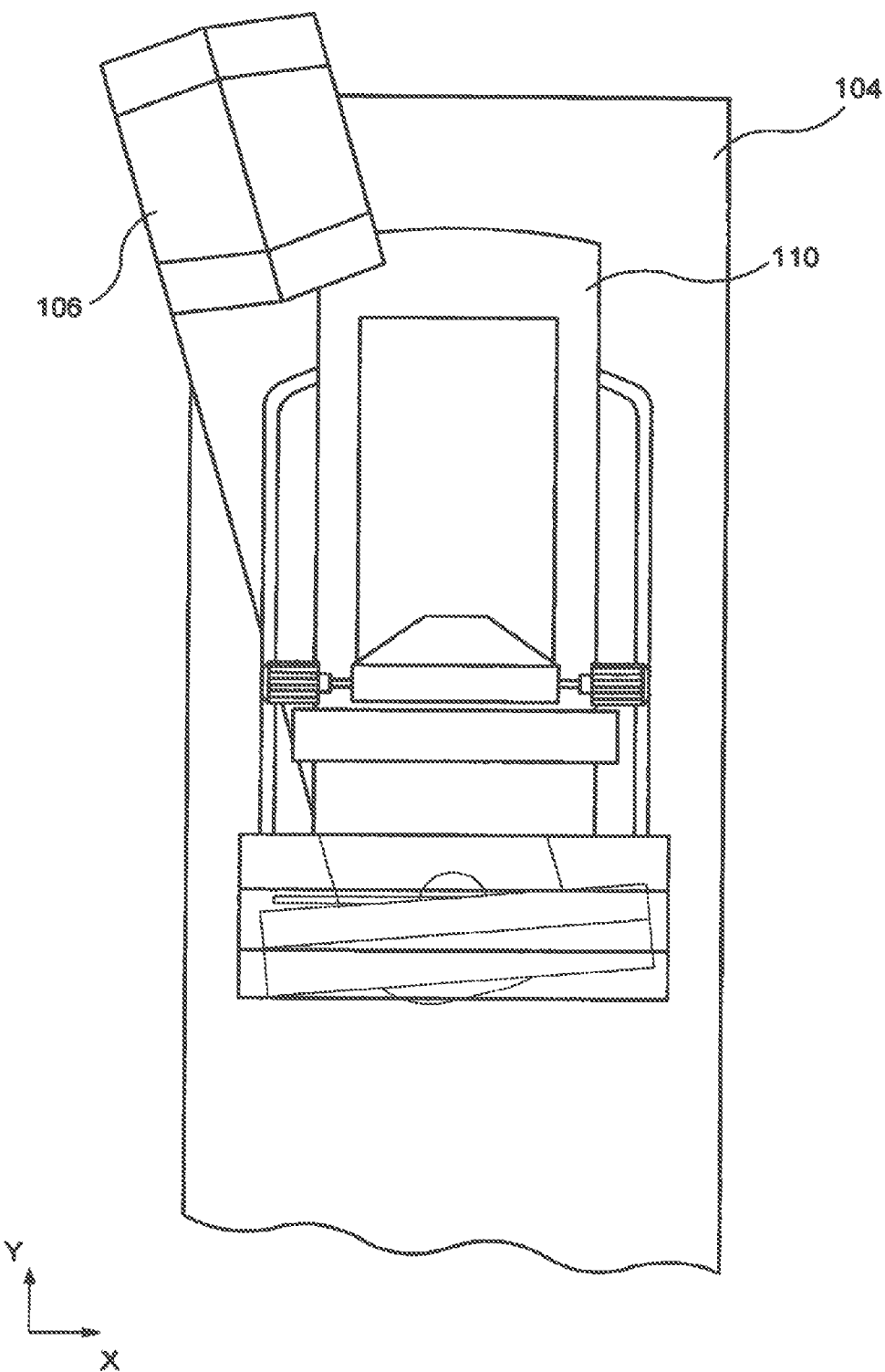
FIG. 3 is a front elevation of the apparatus of FIG. 2.
Figure 4:
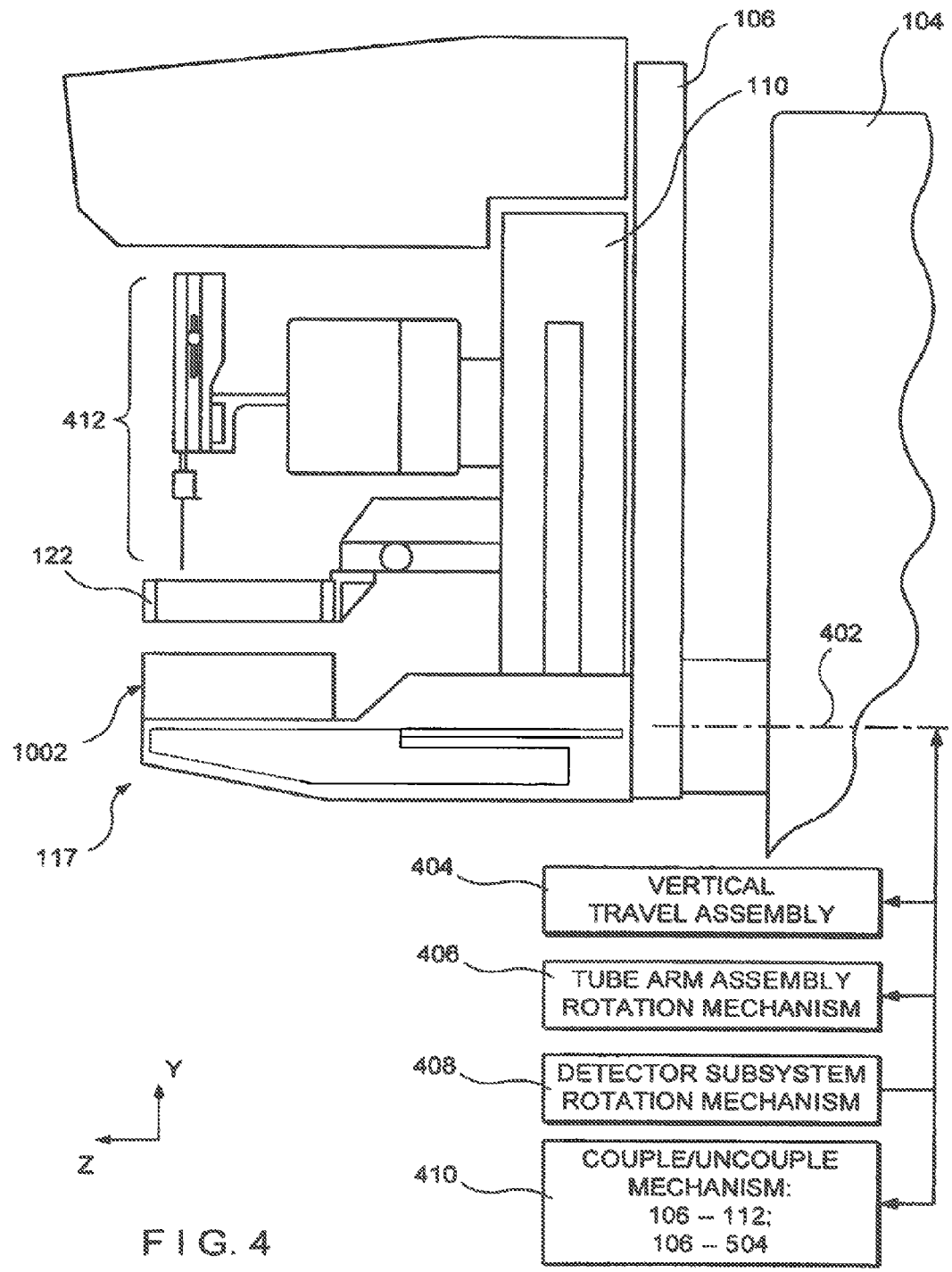
FIG. 4 is a side view of a gantry with a biopsy station and a spacer, with schematic illustration of other mechanisms.
Figure 11:
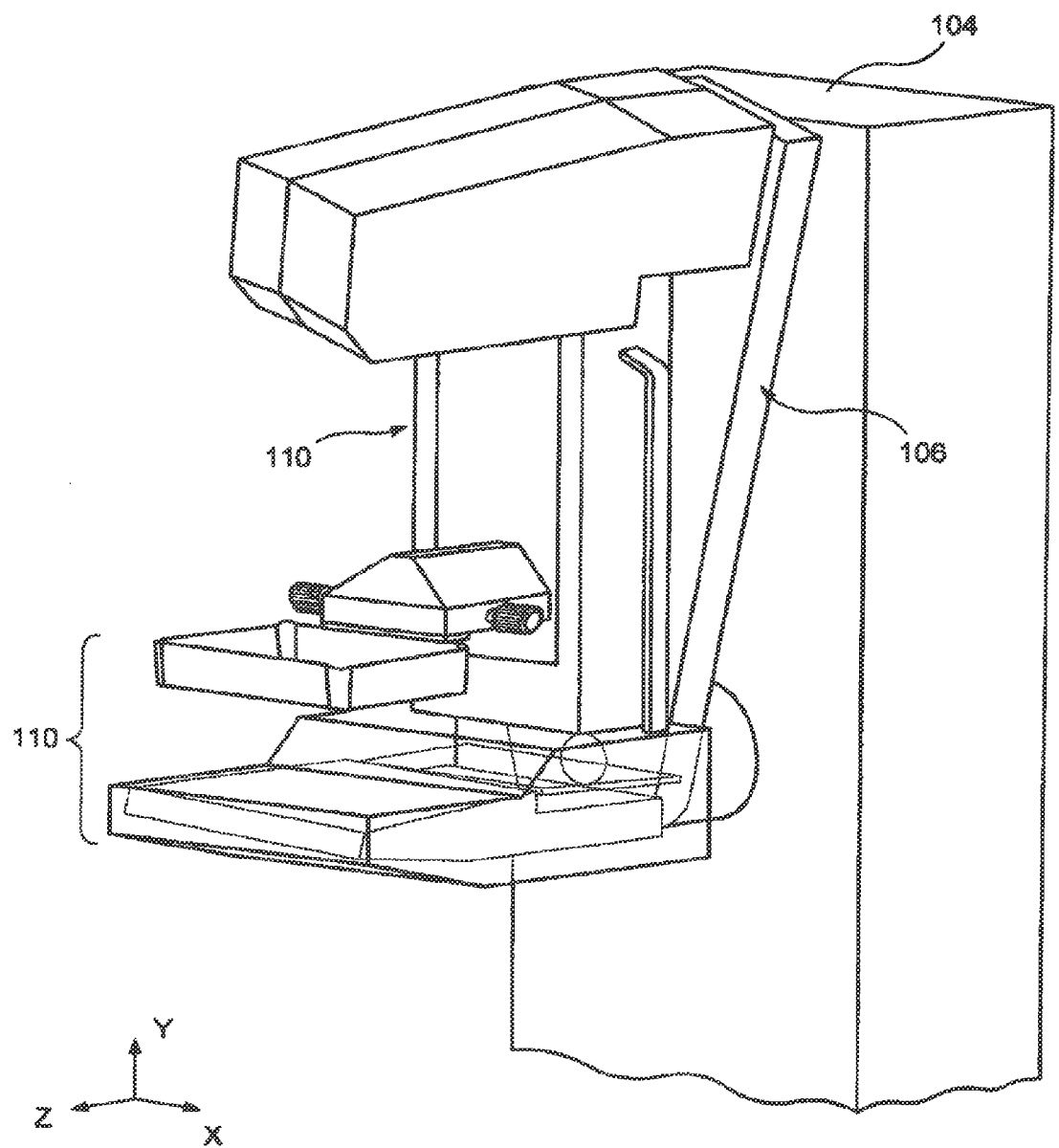
FIG. 11 is similar to FIG. 2 but shows a tube arm assembly angled differently.
Figure 12:
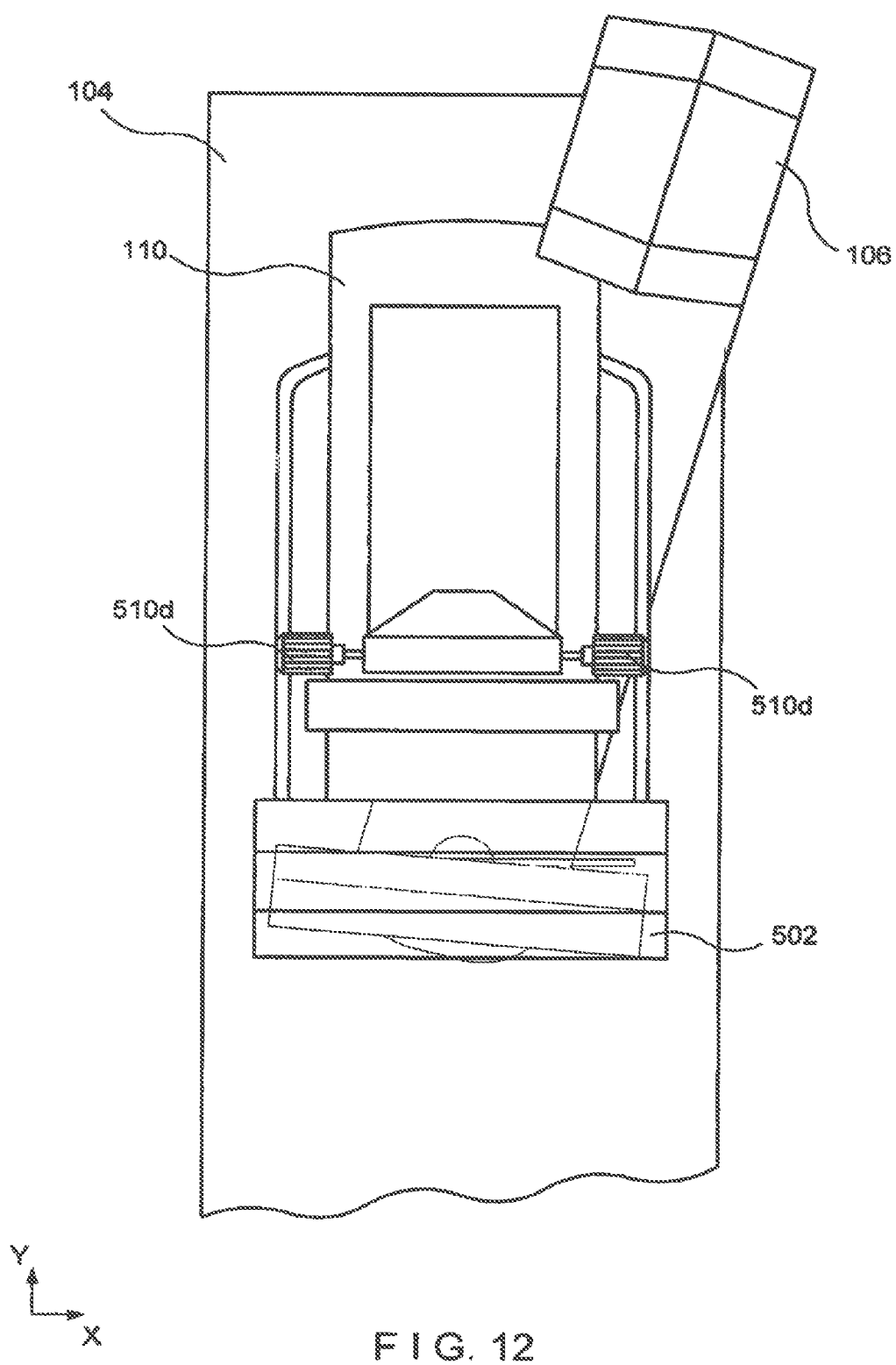
FIG. 12 is a front elevation of the structure of FIG. 11.
Figure 13:
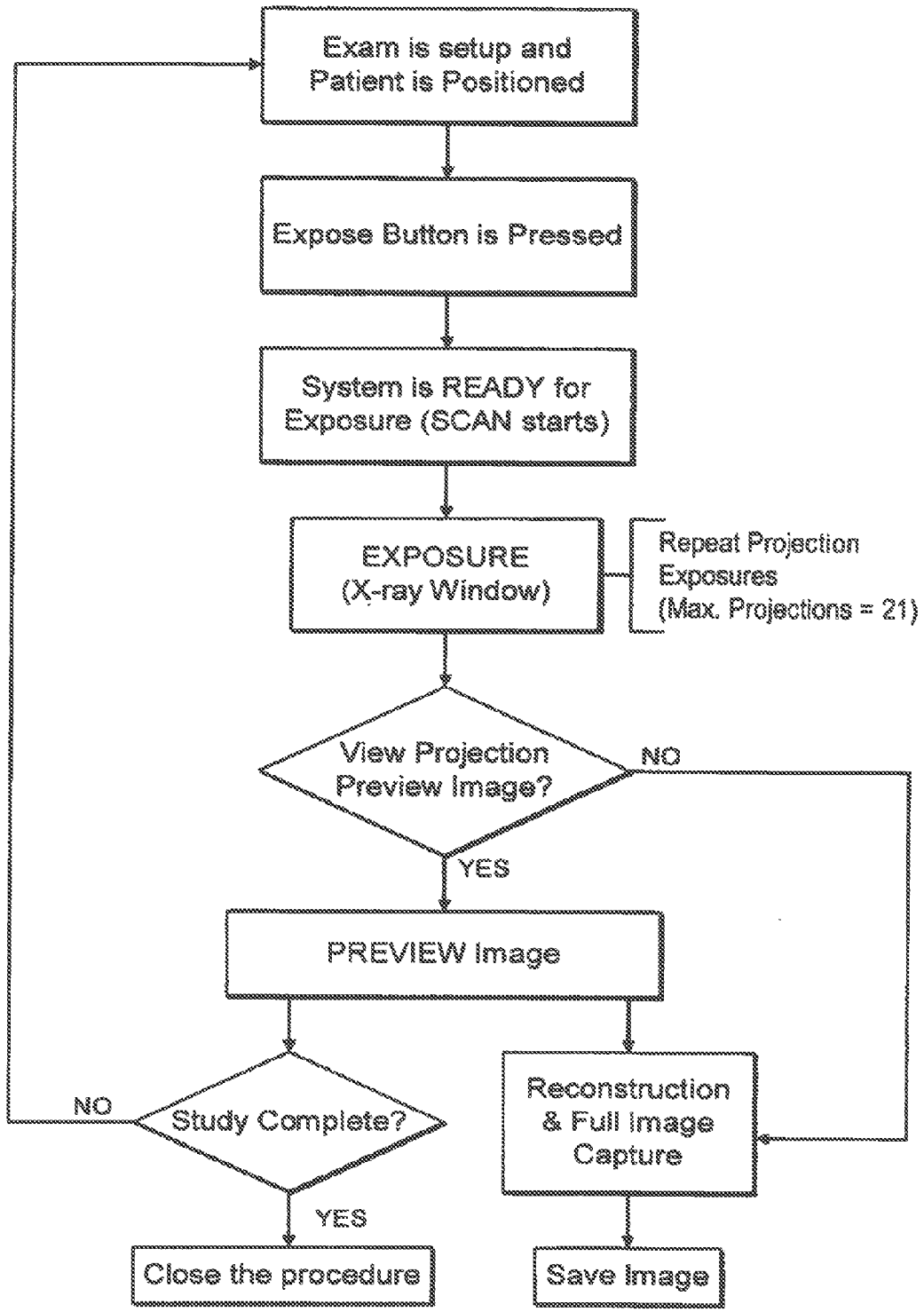
FIG. 13 is a flow chart illustrating one of several examples of work flow for a tomosynthesis mode.
Figure 14:
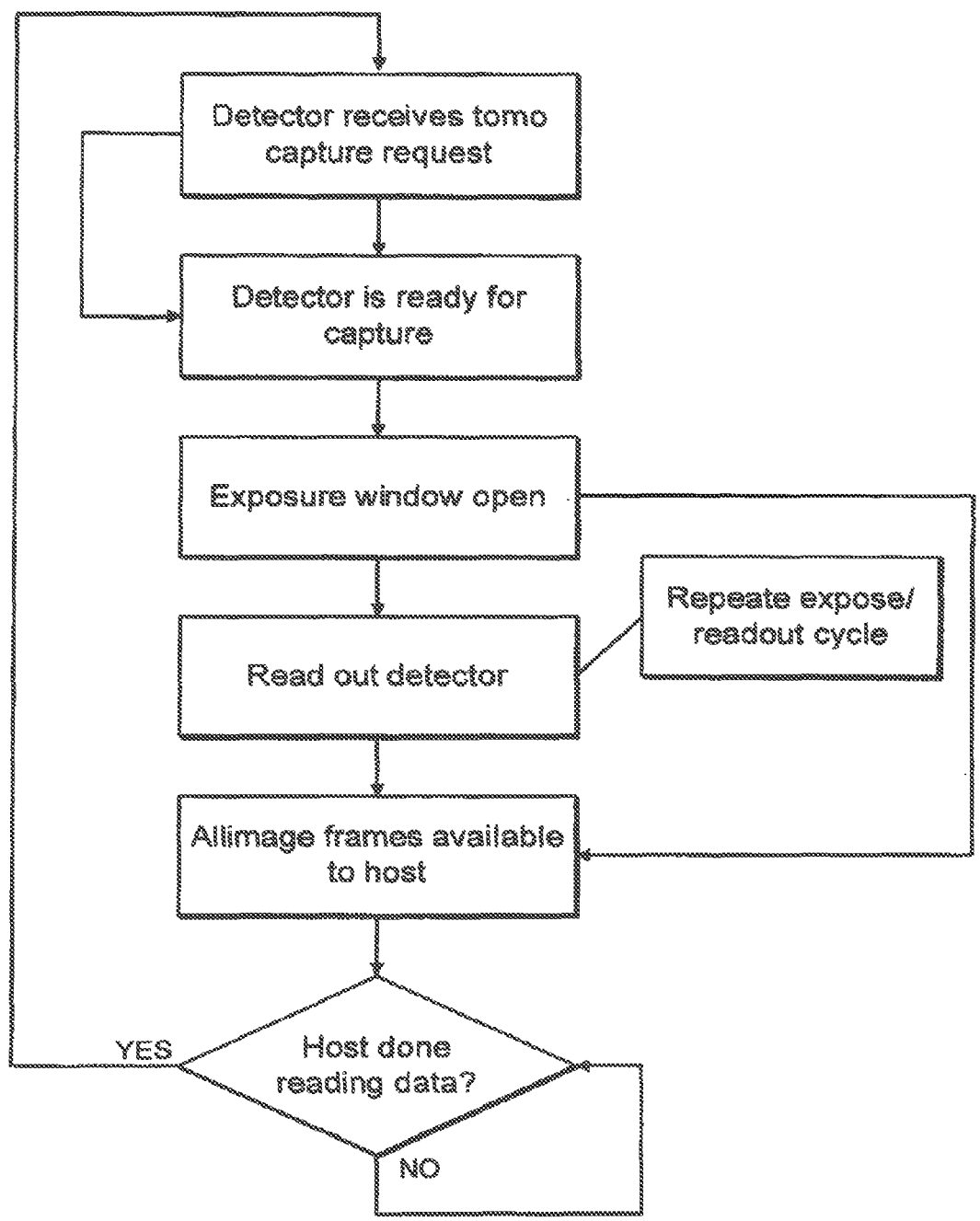
FIG. 14 is a flow chart illustrating one of several examples of work flow for an image detector subsystem in the tomosynthesis mode.

In tomosynthesis mode, tube arm assembly 106 and compression arm assembly 110 are decoupled by unit 410 such that compression arm assembly 110 stays in one position, compressing the patient's breast, while tube arm assembly 106 rotates about axis 402, for example between the position illustrated in FIG. 2 to that illustrated in FIG. 11, or ±15° relative to compression arm assembly 110. Tomosynthesis can be carried out for different image orientations, so that compression arm assembly 110 can be rotated about axis 402 (alone or together with assembly 106) for a desired image orientation and locked in place, and then tube arm assembly 106 can be rotated relative to that position of compression arm assembly 110 for tomosynthesis imaging over ±15° or some other desired angular range. In one example, 11 images are taken during an angular sweep of tube arm assembly 106, one every approximately 3°. However, a different number of images can be taken, for example up to 21 during a single sweep. For tomosynthesis images, the x-ray tube in x-ray tube assembly 108 continuously rotates and the x-ray tube is pulsed for each image, for example, for x-ray energy pulses each lasting approximately 100 mSec, although pulses of different duration can be selected. Alternatively, the rotational motion can stop for taking each image, or continuous motion without pulsing can be used (and the timing of data measurements relied to define pixel values). As seen in FIGS. 2, 3, 5, 11 and 12, in this mode mechanism 506 fully retracts anti-scatter grid 504 away from x-ray receptor 502 so grid 504 is out of the image. Also as seen in these Figs., while the breast remains immobilized in compression arm assembly 110 during the angular sweep of tube arm assembly 106, x-ray receptor 502 rocks within receptor housing 114. In this rocking motion, controlled by unit 408 (FIG. 4), a line normal to the image face of x-ray receptor 502 may keep pointing to the focal spot of the x-ray tube in x-ray tube assembly 108. Alternatively, the rotation of tube arm assembly 106 and rocking of x-ray receptor 502 can be through different angles; for example, tube arm assembly 106 can rotate through 15° while x-ray receptor 502 rocks through 5°, i.e. the rocking angle can be an amount one-third that of assembly 108. Synchronous rotation of tube arm assembly 106 and rocking of x-ray receptor 502 can be achieved by controlling separate motors for each or, alternatively, through using a motor to drive tube arm assembly 106 and a mechanical coupling between the rotation of tube arm assembly 106 and rocking of x-ray receptor 502. Image data can be obtained and processed into tomosynthesis images for display and/or storage as described in the material incorporated by reference, for example in co-pending patent application Ser. No. 10/723, 486 or in U.S. Provisional Application No. 60/628,516, filed Nov. 15, 2004. FIG. 13 illustrates a typical workflow for tomosynthesis mode operation, and FIG. 14 illustrates an example of the operation of detector subsystem 117 in that mode. Again, these are only examples, and other steps or orders of steps can be used instead.

Figure 15:
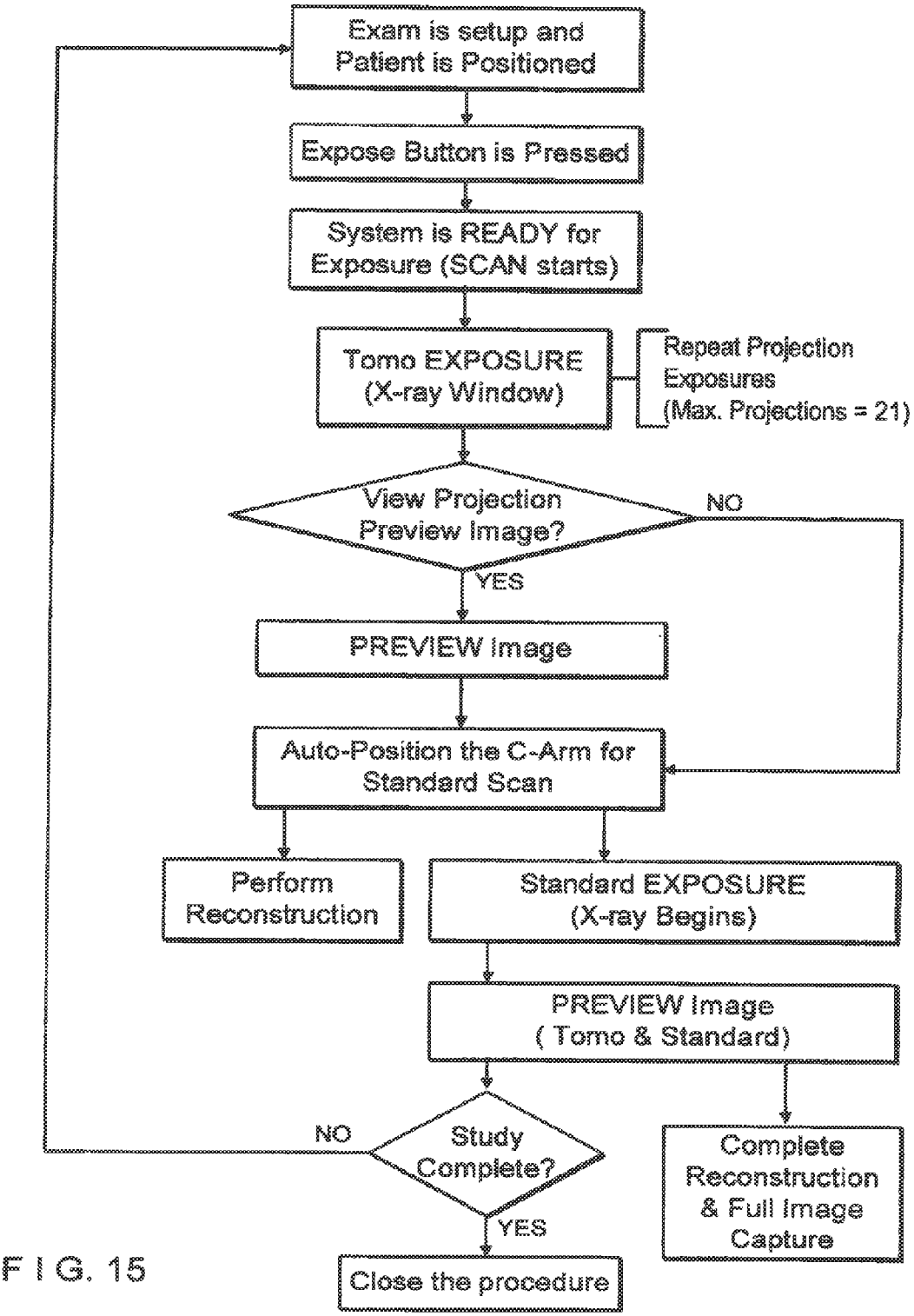
FIG. 15 is a flow chart illustrating one of several examples of work flow for a combination mode.
Figure 16:
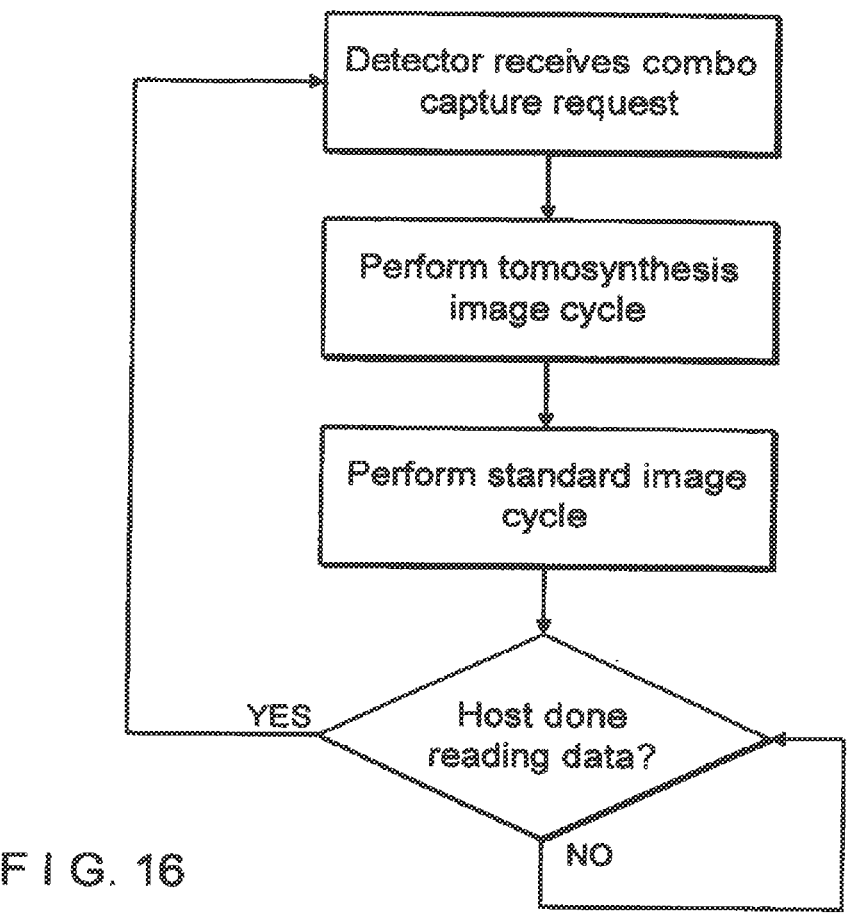
FIG. 16 is a flow chart illustrating one of several examples of work flow for an image detector subsystem in the combination mode.

In a combination mode, during a single compression of the patient's breast the system takes a conventional mammogram and tomosynthesis images. In this mode, while the breast remains compressed in compression arm assembly 110, (1) tube arm assembly 106 sweeps and x-ray receptor 502 rocks, each through an appropriate angle, and exposures are taken for tomosynthesis images, and (2) a standard mammogram is taken. The standard mammogram can be taken at a 0° relative angle between tube arm assembly 106 and a normal to the imaging plane of x-ray receptor 502, and can be taken before or after the tomosynthesis images are taken or between the taking of two successive tomosynthesis images. Typically, each tomosynthesis image utilizes substantially lower x-ray dose than the standard mammogram. For example, the total x-ray dosage for tomosynthesis imaging in one sweep of tube arm assembly 106 can be approximately the same as that for a single standard mammogram, or up to approximately three times that dosage. The relationship between the two dosages can be user-selected. FIG. 15 illustrates an example of workflow for the combination mode, and FIG. 16 illustrates an example of the operation of detector subsystem 117 in that mode. Again, these are examples, and different steps or orders of steps can be used instead. For example, a preferred approach may be to take the standard mammogram first, then move arm 106 to one end of its rotational range for tomosynthesis and take the tomosynthesis images. The order in which the two types of images are taken may be optimized such that the overall imaging time is minimized, and an order that achieves such minimization can be the preferred order. The exposure (tube current mA, tube voltage kVp, and exposure length msec) techniques for the standard mammogram and the tomosynthesis exposures can be set manually, or by using automatic methods. If the standard mammogram is taken first, its exposure techniques can be used to set an optimal technique for the subsequent tomosynthesis images, and vice versa. The exposure technique can be modified dynamically, if the software senses that the signal reaching the image receptor is either too low or too high and adjust subsequent exposures as needed.

In a stereotactic mode, during a single compression of the patient's breast at least two images of taken, for example one at (±15)° angle and one at (−15°) angle of tube arm assembly 106 relative to compression arm assembly 110, although other angles can be used and more images can be taken. X-ray receptor 502 can remain in place for this procedure, or can be rocked through a selected angle, for example through an angle sufficient to maintain the same orientation of the imaging surface of receptor 502 relative to tube arm assembly 106. A spacer 1002 can be used for magnification. If x-ray receptor 502 remains in place despite rotation of arm 106, or if spacer 1002 is used, anti-scatter grid 504 is fully retracted; if x-ray receptor 502 maintains its orientation relative to tube arm assembly 106 and not spacer 1002 is used, anti-scatter grid 504 need not be retracted. As is known in the art, the two or more images can be used to identify the location of a lesion, so that needle biopsy can be used, for example with an upright needle biopsy station 412 (FIG. 4) in a manner similar to that used with the commercially available Selenia™ system and StereoLoc II™. A compression paddle 122 appropriate for needle biopsy typically is used when taking the stereotactic images, Alternatively, some or all of the images taken in the tomosynthesis mode and/or in the combined mode can be used to identify the location of a lesion for biopsy, in which case a compression paddle 122 appropriate for the purpose typically is used when taking the images.

In needle localization mode, x-ray images can be taken after a biopsy or other needle is inserted into the compressed breast. For this purpose, imaging such as in the stereotactic mode, the tomosynthesis mode, or the combined mode can be used.

In the disclosed system, compression paddle 122 is movable laterally, as generally described in U.S. Patent Application Publication No. 2005/0063509 A1, hereby incorporated by reference herein. In addition, compression paddle 122 can pivot about an axis along the patient's chest wall to conform the breast shape in certain procedures, as discussed in said U.S. Pat. No. 5,706,327. However, in the system of this patent specification compression paddle 122 is mounted differently and moves in a different manner.

Figure 5:
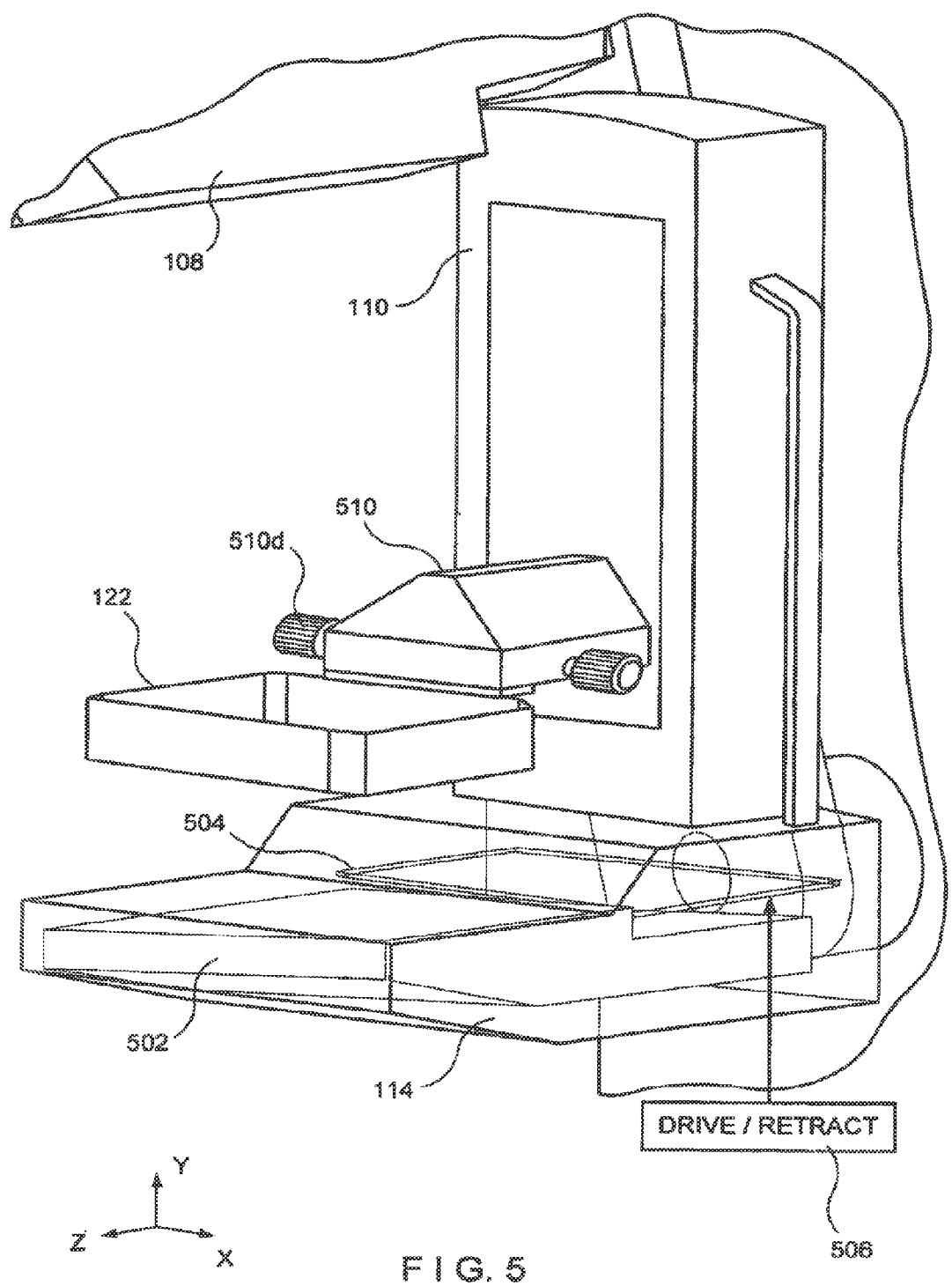
FIG. 5 is an enlarged view of a portion of FIG. 1.
Figure 17:
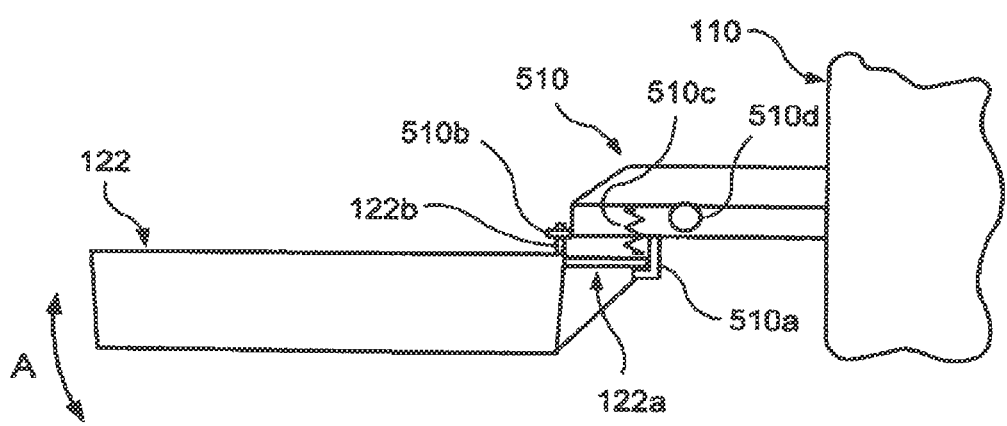
FIG. 17 is an enlarged side view of a structure for removably mounting a breast compression paddle.

As illustrated in FIGS. 5 and 17, compression paddle 122 is removably mounted to a support 510 that moves up and down compression arm assembly 110 as needed for breast compression. To mount compression paddle 122 onto 510, a projection compression paddle 122a of the paddle engages a projection 510a of the support, and a projection 122b of the paddle latches onto projection 510b of the support. Projection 510a is spring-loaded, such as by a spring schematically illustrates at 510c to allow for pivoting compression paddle 122 about an axis where it latches onto 510, as illustrated by arrow A, for better conformance with the compressed breast in some imaging protocols. Other imaging protocols may require compression paddle 122 not to pivot, in which case projection 510a is locked in place by a locking mechanism in 510 (not shown) to keep compression paddle 122 in place relative to support 510. The locking mechanism can be manually set to a lock position, and manually unlocked by the operator. Alternatively, the locking mechanism can be controlled through an operator input at gantry 100 or workstation 102. A sensing mechanism can be included to sense whether compression paddle 122 is locked against pivoting, to provide information that work-station 102 can use for setting imaging protocols such as for automated breast compression and automated exposure methods. Two knobs 510d, one on each lateral side of support 510, can be manually rotated to move projection 510b and thus compression paddle 122 laterally such that it compress a breast that is not centered laterally on upper surface 116, for example for MLO imaging. Each knob 510d can operate a mechanism such as an endless screw rotating in a nut secured to projection 510b. Alternatively, or in addition, projection 510b and thus compression paddle 122 can be driven laterally by a motor, under control of operator switches or other interface at gantry 100 or at workstation 102, or automatically positioned laterally under computer control.

Importantly, compression paddle 122 is driven for lateral movement by components that are a part of support 510. Thus, compression paddle 122 can be simple structure, and can even be disposable, with a new one used for each patient or for only a few patients. This can simplify and reduce the cost of using the system, because an imaging facility usually stocks a number of different paddles for different purposes. If the lateral movement mechanism is integral with a compression paddle, the paddle assembly is considerably larger, heavier and more expensive. But with a compression paddle 122 that relies for lateral movement on support 510, and is easily mounted by hand and without tools to support 510, by sliding compression paddle 122a into projection 510a and latching projection paddle 122b onto projection 510b, and is easily removed by reversing the process, the expense of keeping a number of different compression paddles in stock or replacing paddles with new ones is greatly reduced, as are the time and convenience when changing from one type of compression paddle to another. Compression paddle 122 can include a bar code that is automatically read by a bar code reader in support 510, to keep work-station 102 informed of the paddle currently mounted to support 510, for use in automating imaging protocols. For example, the bar code information can be checked to ensure through computer processing that the type of paddle that is currently mounted on support 510 matches the imaging that will be commanded, and the information from the sensor for whether compression paddle 122 is locked in non-tilting mode can be used to automatically make adjustments for compression height to ensure accurate automatic x-ray exposure operation. Further, the bar code information identifying the paddle can be used to automatically set collimation in x-ray tube assembly 108 so that the x-ray beam matches the size and shape of the currently installed compression paddle 122.

The above specific examples and embodiments are illustrative, and many variations can be introduced on these examples and embodiments without departing from the spirit of the disclosure or from the scope of the appended claims. For example, elements and/or features of different illustrative embodiments may be combined with each other and/or substituted for each other within the scope of this disclosure and appended claims.

This application claims the benefit of U.S. provisional application Ser. No. 60/631,296, filed Nov. 26, 2004 and entitled "INTEGRATED MULTI-MODE MAMMOGRAPHY/TOMOSYNTHESIS X-RAY SYSTEM AND METHOD", the entire contents of which are incorporated herein by reference.

The invention claimed is:

1. A system for multi-mode breast x-ray imaging comprising:
a compression arm assembly for compressing and immobilizing a patient's breast for x-ray imaging, the compression arm assembly comprising a breast compression paddle;
an x-ray tube assembly; and
an x-ray image receptor, wherein the compression arm assembly, the x-ray tube assembly, and the x-ray image receptor are configured for movement to accommodate a plurality of imaging modes, wherein the x-ray tube assembly is configured to rotate relative to the breast compression paddle about an axis for at least one of the plurality of imaging modes, and
wherein the breast compression paddle is configured to move laterally relative to the x-ray image receptor, and wherein at least two or more of the plurality of imaging modes utilize the same breast compression.

2. The system of claim 1, wherein one of the plurality of imaging modes is a conventional mammography imaging mode in which the x-ray tube assembly and the x-ray image receptor are fixed relative to one another.

3. The system of claim 1 further comprising an anti-scatter grid disposed between the breast compression paddle and the x-ray image receptor for at least one of the plurality of imaging modes.

4. The system of claim 3, wherein the anti-scatter grid is retractable out of the imaging area for at least one of the plurality of imaging modes.

5. The system of claim 1, wherein two of the plurality of imaging modes comprise a standard mammography imaging mode and a tomosynthesis imaging mode.

6. The system of claim 1, wherein the compression paddle is centered on the x-ray receptor for a CC view of a breast and moved to one lateral side of the x-ray receptor for an MLO view of the breast.

7. The system of claim 1, wherein the compression paddle is removably coupled to the system.

8. The system of claim 1, wherein the compression paddle is configured to tilt such that the compression paddle is not parallel to the x-ray receptor.

9. The system of claim 8, wherein the compression paddle is lockable in a tilted position such that the compression is not parallel to the x-ray receptor.

10. The system of claim 1, wherein the x-ray tube assembly moves continuously for image acquisition when the x-ray tube assembly rotates relative to the breast compression paddle about the axis.

11. The system of claim 1, wherein the x-ray tube assembly can stop for each image acquisition when the x-ray tube assembly rotates relative to the breast compression paddle about the axis.

12. A system for multi-mode breast x-ray imaging comprising:
a compression arm assembly for compressing and immobilizing a patient's breast for x-ray imaging, the compression arm assembly comprising a breast compression paddle;
an x-ray tube assembly; and
an x-ray image receptor, wherein the compression arm assembly, the x-ray tube assembly, and the x-ray image receptor are configured for movement to accommodate a plurality of imaging modes, wherein the x-ray tube assembly is configured to rotate relative to the breast compression paddle about an axis for at least one of the plurality of imaging modes, and
wherein the breast compression paddle is configured to move laterally relative to the x-ray image receptor, and wherein the compression paddle is configured to tilt such that the compression paddle is not parallel to the x-ray receptor.

13. The system of claim 12, wherein the compression paddle is lockable in a tilted position such that the compression is not parallel to the x-ray receptor.

14. The system of claim 12, wherein one of the plurality of imaging modes is a conventional mammography imaging mode in which the x-ray tube assembly and the x-ray image receptor are fixed relative to one another.

15. The system of claim 12 further comprising an anti-scatter grid disposed between the breast compression paddle and the x-ray image receptor for at least one of the plurality of imaging modes.

16. The system of claim 15, wherein the anti-scatter grid is retractable out of the imaging area for at least one of the plurality of imaging modes.

17. The system of claim 12, wherein at least two or more of the plurality of imaging modes utilize the same breast compression.

18. The system of claim 17, wherein two of the plurality of imaging modes comprise a standard mammography imaging mode and a tomosynthesis imaging mode.

19. The system of claim 12, wherein the x-ray tube assembly can stop for each image acquisition when the x-ray tube assembly rotates relative to the breast compression paddle about the axis.

* * * * *